(12) United States Patent
Ferek-Petric et al.

(10) Patent No.: US 7,037,266 B2
(45) Date of Patent: May 2, 2006

(54) ULTRASOUND METHODS AND IMPLANTABLE MEDICAL DEVICES USING SAME

(75) Inventors: Bozider Ferek-Petric, Zegreb (HR); Branko Breyer, Zegreb (HR)

(73) Assignee: Medtronic, Inc., Minneapolis, MN (US)

( * ) Notice: Subject to any disclaimer, the term of this patent is extended or adjusted under 35 U.S.C. 154(b) by 397 days.

(21) Appl. No.: 10/131,256

(22) Filed: Apr. 25, 2002

(65) Prior Publication Data

US 2003/0204140 A1   Oct. 30, 2003

(51) Int. Cl.
*A61B 8/06* (2006.01)

(52) U.S. Cl. ..................................................... 600/453

(58) Field of Classification Search ........ 600/437–472; 607/4, 9, 14, 17, 22, 27; 604/22; 601/2, 601/3

See application file for complete search history.

(56) References Cited

U.S. PATENT DOCUMENTS

| | | | |
|---|---|---|---|
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallock |
| 4,800,883 A | 1/1989 | Winstrom |
| 4,821,723 A | 4/1989 | Baker, Jr. et al. |
| 4,830,006 A | 5/1989 | Haluska et al. |
| 4,880,005 A | 11/1989 | Pless et al. |
| 4,890,617 A | 1/1990 | Markowitz et al. |
| 4,949,719 A | 8/1990 | Pless et al. |
| 4,953,551 A | 9/1990 | Mehra et al. |
| 5,099,838 A | 3/1992 | Bardy |
| 5,117,824 A | 6/1992 | Keimel et al. |
| 5,131,388 A | 7/1992 | Pless |
| 5,144,949 A | 9/1992 | Olson |
| 5,158,078 A | 10/1992 | Bennett et al. |
| 5,163,427 A | 11/1992 | Keimel |

(Continued)

FOREIGN PATENT DOCUMENTS

WO    WO92/18198    10/1992

OTHER PUBLICATIONS

Arzbaecher et al., "Automatic Tachycardia Recognition", *PACE*, 541-547 (May-Jun. 1984).

(Continued)

*Primary Examiner*—Ali Imam
(74) *Attorney, Agent, or Firm*—Paul H. McDowall; Girma Wolde-Michael

(57) ABSTRACT

An ultrasound method and medical devices using same provide for various techniques of sampling blood flow velocity, e.g., at several sampling rates. To minimize the energy required for ultrasound monitoring, pulsed Doppler signal packages provided by a pulsed ultrasound circuit are switched in such a way that the repetition rate is the lowest possible and yet sufficiently high to be able to record the blood flow velocity within the heart. For example, an ultrasound circuit may be activated only within a part of the cardiac cycle designated as the Doppler Measurement Interval (DMI); the ultrasound circuit may be switched between an on state and an off state during the DMI; and/or the ultrasound circuit may also be switched on and off in different sampling modes: detection mode and measurement mode (e.g., using different sampling rates).

40 Claims, 18 Drawing Sheets

U.S. PATENT DOCUMENTS

| | | |
|---|---|---|
| 5,183,040 A | 2/1993 | Nappholz et al. |
| 5,186,175 A * | 2/1993 | Hirama et al. .............. 600/447 |
| 5,188,105 A | 2/1993 | Keimel |
| 5,199,428 A | 4/1993 | Obel et al. |
| 5,207,218 A | 5/1993 | Carpentier et al. |
| 5,243,976 A | 9/1993 | Ferek-Petric et al. |
| 5,269,298 A | 12/1993 | Adams et al. |
| 5,312,453 A | 5/1994 | Shelton et al. |
| 5,314,430 A | 5/1994 | Bardy |
| 5,316,001 A | 5/1994 | Ferek-Petric et al. |
| 5,318,595 A | 6/1994 | Ferek-Petric et al. |
| 5,330,507 A | 7/1994 | Schwartz |
| 5,331,966 A | 7/1994 | Bennett et al. |
| 5,354,316 A | 10/1994 | Keimel |
| 5,545,186 A | 8/1996 | Olson et al. |
| 5,690,686 A | 11/1997 | Min et al. |
| 5,800,465 A | 9/1998 | Thompson et al. |

OTHER PUBLICATIONS

Olson et al., "Onset and Stability for Ventricular Tachyarrhythmia Detection in an Implantable Pacer-Cardioverter-Defibrillator," *Computers in Cardiology*, IEEE Computer Society Press, 167-170 (Oct. 7-10, 1986).

* cited by examiner

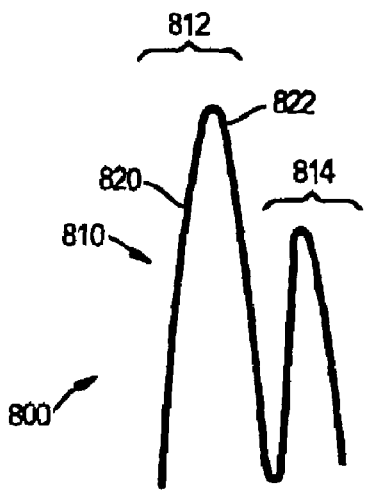
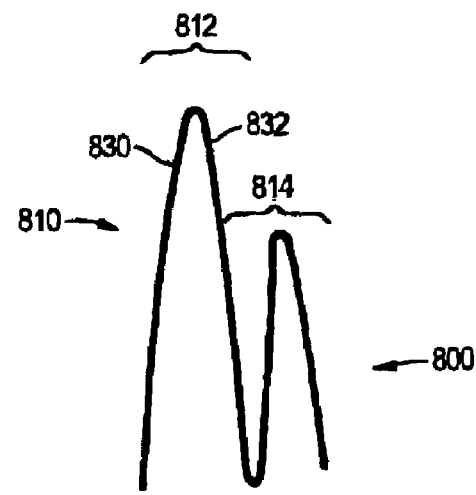
FIG. 13a     FIG. 13b
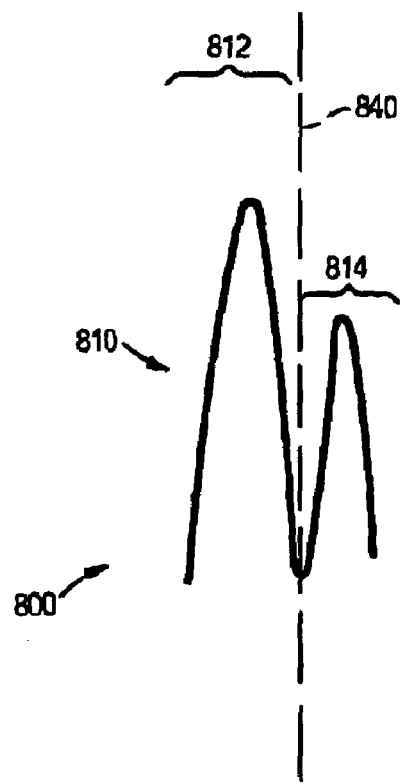
FIG. 13c

ULTRASOUND METHODS AND IMPLANTABLE MEDICAL DEVICES USING SAME

FIELD OF THE INVENTION

The present invention relates to cardiac therapy. More particularly, the present invention pertains to the use of ultrasound in the measurement of blood flow velocity such as for use in control of such therapy.

BACKGROUND

The utility of measuring blood flow velocity, e.g., at a region proximate a tricuspid valve of a heart, such as for the purpose of cardiac pacing and control has been described in the art. For example, U.S. Pat. No. 5,243,976 to Ferek-Petric entitled "Tricuspid Flow Synchronized Cardiac Electrotherapy System with Blood Flow Measurement Transducer and Controlled Pacing Signals Based on Blood Flow Measurement," issued Sep. 14, 1993, and U.S. Pat. No. 5,316,001 to Ferek-Petric et al. entitled "Cardiac Measurement System for Measuring Blood Flow Velocity by Use of a Sensor Implanted Inside the Heart," issued May 31, 1994, disclose the utility of pulsed wave and continuous wave Doppler methods for blood flow velocity measurement within the tricuspid valve. An implantable lead design was also described that emphasized a Doppler sensitive volume of blood flow. Further, U.S. Pat. No. 5,318,595 to Ferek-Petric et al. entitled "Pacing Method and System for Blood Flow Velocity Measurement and Regulation of Heart Stimulating Signals Based on Blood Flow Velocity," issued Jun. 7, 1994, discloses a method of the closed loop A-V interval regulation.

Although continuous wave Doppler methods provide continuous monitoring of blood flow velocity, the method may undesirably deplete the stored energy of IMD power sources. Further, continuous wave Doppler methods may not have the depth resolution and range accuracy of pulsed wave Doppler methods.

Pulsed Doppler ultrasound is an accurate method of measuring blood flow velocity. However, pulsed Doppler ultrasound is not very convenient for implantable medical devices (IMDs) because of the limited energy storage available in today's power sources.

Table 1 below lists U.S. patents relating to various ultrasound techniques.

TABLE 1

| Patent No. | Inventor | Issue Date |
|---|---|---|
| 5,183,040 | Nappholz et al. | Feb. 2, 1993 |
| 5,243,976 | Ferek-Petric et al. | Sep. 14, 1993 |
| 5,316,001 | Ferek-Petric et al. | May 31, 1994 |
| 5,318,595 | Ferek-Petric et al. | Jun. 7, 1994 |

All documents listed in Table 1 above and further elsewhere herein are hereby incorporated by reference herein in their respective entireties. As those of ordinary skill in the art will appreciate readily upon reading the Summary of the Invention, Detailed Description of the Embodiments, and claims set forth below, many of the devices and methods disclosed in the documents of Table 1 and other documents incorporated by reference herein may be modified advantageously by using the teachings of the present invention.

SUMMARY OF THE INVENTION

The present invention has certain objects. That is, various embodiments of the present invention provide solutions to one or more problems existing in the art with respect to ultrasound methods utilized with IMDs. One such problem involves the demand on battery life that current Doppler ultrasound techniques place on IMD power sources.

In comparison to known techniques for IMDs, various embodiments of the present invention may provide certain advantages. For instance, conservation of battery power may be achieved by limiting the time that ultrasound circuitry is utilized to sample blood flow velocity while providing enough sampled data to accurately record a blood flow velocity.

Some embodiments of methods according to the present invention may provide one or more of the following features for measuring fluid flow velocity: activating an ultrasound circuit during a first portion of at least one cardiac cycle, wherein the ultrasound circuit is operable to provide pulsed Doppler signal packages during the first portion of the at least one cardiac cycle; deactivating an ultrasound circuit during a second portion of the at least one cardiac cycle, wherein the ultrasound circuit is inoperable to provide pulsed Doppler signal packages during the second portion of the at least one cardiac cycle; switching an ultrasound circuit between an on state where pulsed Doppler signal packages are provided and an off state where pulsed Doppler signal packages are not provided during a first portion of at least one cardiac cycle at a first sampling rate; switching an ultrasound circuit between an on state and off state at a first sampling rate during at least a first time period of a first portion of the at least one cardiac cycle; switching an ultrasound circuit between an on state and an off state at a second rate during at least a second time period of a first portion of at least one cardiac cycle; switching an ultrasound circuit between an on state and off state at a first sampling rate during at least a first portion of a first cardiac cycle and thereafter switching the ultrasound circuit between an on state and an off state during a first portion of at least another cardiac cycle at a second rate; detecting a rate switching event; switching from a first rate to a second rate based on detection of a rate switching event; detecting a rate switching event based on a monitored physiological parameter; switching from a second rate to a first rate based on detection of an additional rate switching event; selecting a frequency of the provided pulsed Doppler signal packages based on a predetermined maximum blood flow velocity; pacing a heart based at least on the sampled blood flow velocity; monitoring a heart rate; detecting a rate switching event based on monitored heart rate; sampling a diastolic blood flow velocity filling wave at a sampling rate; determining an acceleration of a diastolic blood flow velocity filling wave; detecting tachycardia if an acceleration of a diastolic blood flow velocity filling wave satisfies a diastolic blood flow velocity filling wave acceleration threshold; and delivering a therapy upon detecting tachycardia; activating an ultrasound circuit during at least a first time interval, wherein the ultrasound circuit is operable to provide pulsed Doppler signal packages during the first time interval; deactivating an ultrasound circuit during at least a second time interval, wherein the ultrasound circuit is inoperable to provide pulsed Doppler signal packages during the second time interval; switching an ultrasound circuit between an on state where pulsed Doppler signal packages are provided and an off state where pulsed Doppler signal packages are not provided during at least a portion of a first time interval at a first rate (e.g., the ultrasound circuit being deactivated during the second time interval); and sampling blood flow velocity during a time interval of each cardiac cycle of a plurality of cardiac cycles, wherein the time interval of the cardiac cycle sampled varies within each subsequent cardiac cycle of the plurality of cardiac cycles.

Further, some embodiments of the apparatus or systems according to the present invention include one or more of the following features: an IMD; an ultrasound circuit operable to provide pulsed Doppler signal packages; controller circuitry in communication with ultrasound circuit, controller circuitry operable to activate an ultrasound circuit during at least a first interval, wherein the ultrasound circuit is operable to provide pulsed Doppler signal packages during the first time interval; controller circuitry operable to deactivate an ultrasound circuit during at least a second time interval, wherein the ultrasound circuit is inoperable to provide pulsed Doppler signal packages; controller circuitry operable to switch an ultrasound circuit between an on state where pulsed Doppler signal packages are provided and an off state where pulsed Doppler signal packages are not provided during at least a portion of the first time interval at a first rate, and also the controller circuitry may be operable to switch the ultrasound circuit between an on state and an off state during at least another portion of the first time interval at a second rate; a detection sensor operable to detect a rate switching event; controller circuitry operable to switch from a first rate to a second rate based on detection of a rate switching event; controller circuitry operable to switch between an on state and an off state at a first rate during one or more cardiac cycles; controller circuitry operable to switch between an on state and an off state at a second rate during one or more different cardiac cycles; controller circuitry operable to detect an atrial blood flow velocity filling wave; controller circuitry operable to determine an acceleration of a diastolic blood flow velocity filling wave; controller circuitry operable to switch from a second rate to a first rate based on detection of a rate switching event; a detection sensor operable to detect a rate switching event based on the detected physiological parameter; an ultrasound circuit operable to provide pulsed Doppler signal packages at a frequency based on a predetermined maximum blood flow velocity; an implantable lead operable to deliver pulsed Doppler signal packages to a region proximate a tricuspid valve; sensing circuitry for sensing cardiac activity; controller circuitry operable to sample blood flow velocity during a time interval of each cardiac cycle of a plurality of cardiac cycles, wherein the time interval of the cardiac cycle sampled varies within each subsequent cardiac cycle of the plurality of cardiac cycles; controller circuitry operable to trigger a sampling delay interval upon detection of a QRS complex; and controller circuitry operable to sample blood flow velocity during a time interval after a sampling delay interval.

The above summary of the invention is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

The present invention will be further described with reference to the drawings, wherein:

FIGS. 13a–13c are graphs illustrating exemplary sampling rates for the dual sampling ultrasound method of FIG. 12;

DETAILED DESCRIPTION OF THE EMBODIMENTS

Figure 1:
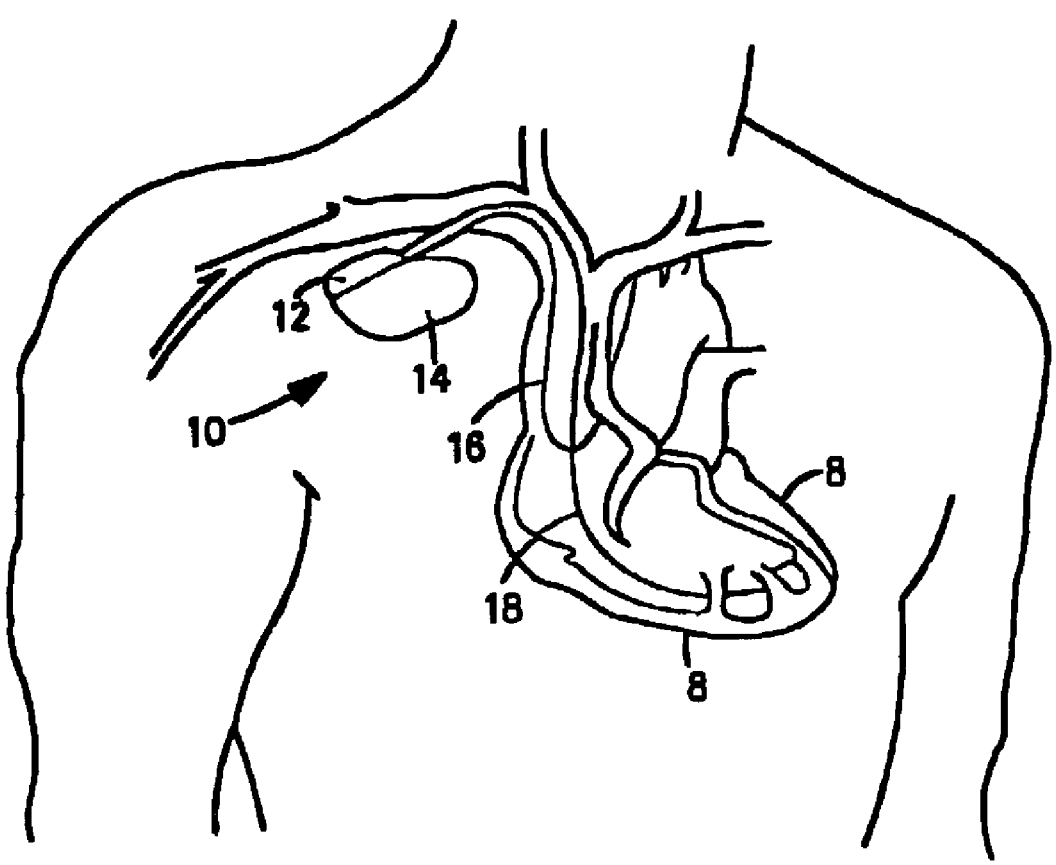
FIG. 1 is an implantable medical device (IMD) in accordance with one embodiment of the invention, wherein the IMD is shown implanted within the body of a patient.

FIG. 1 is a simplified schematic view of one embodiment of implantable medical device ("IMD") 10 of the present invention that may use one or more ultrasound techniques/ methods or devices described herein. For example, the implantable device may include a pulsed Doppler ultrasound circuit in communication with a transducer on an implantable cardiac lead that is implanted in the heart. In order to minimize the energy requirement, which in turn decreases the battery current consumption, pulsed Doppler signal packages provided by the pulsed Doppler ultrasound circuit are switched in such a way that the repetition rate is the lowest possible and yet sufficiently high to be able to record the blood flow velocity within the heart.

Moreover, at least in certain embodiments, the ultrasound circuit may be activated only within a part of the cardiac cycle designated as the Doppler Measurement Interval (DMI). For example, the ultrasound circuit may be switched between an on state and an off state during the DMI and thereby sampling the flow velocity only during a portion of the cardiac cycle yielding an additional decrease of the average power used by the ultrasound technique. The ultrasound circuit may also be switched on and off in different sampling modes: detection mode and measurement mode (e.g., using different sampling rates). These various power saving techniques, and others, are described in further detail herein.

IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
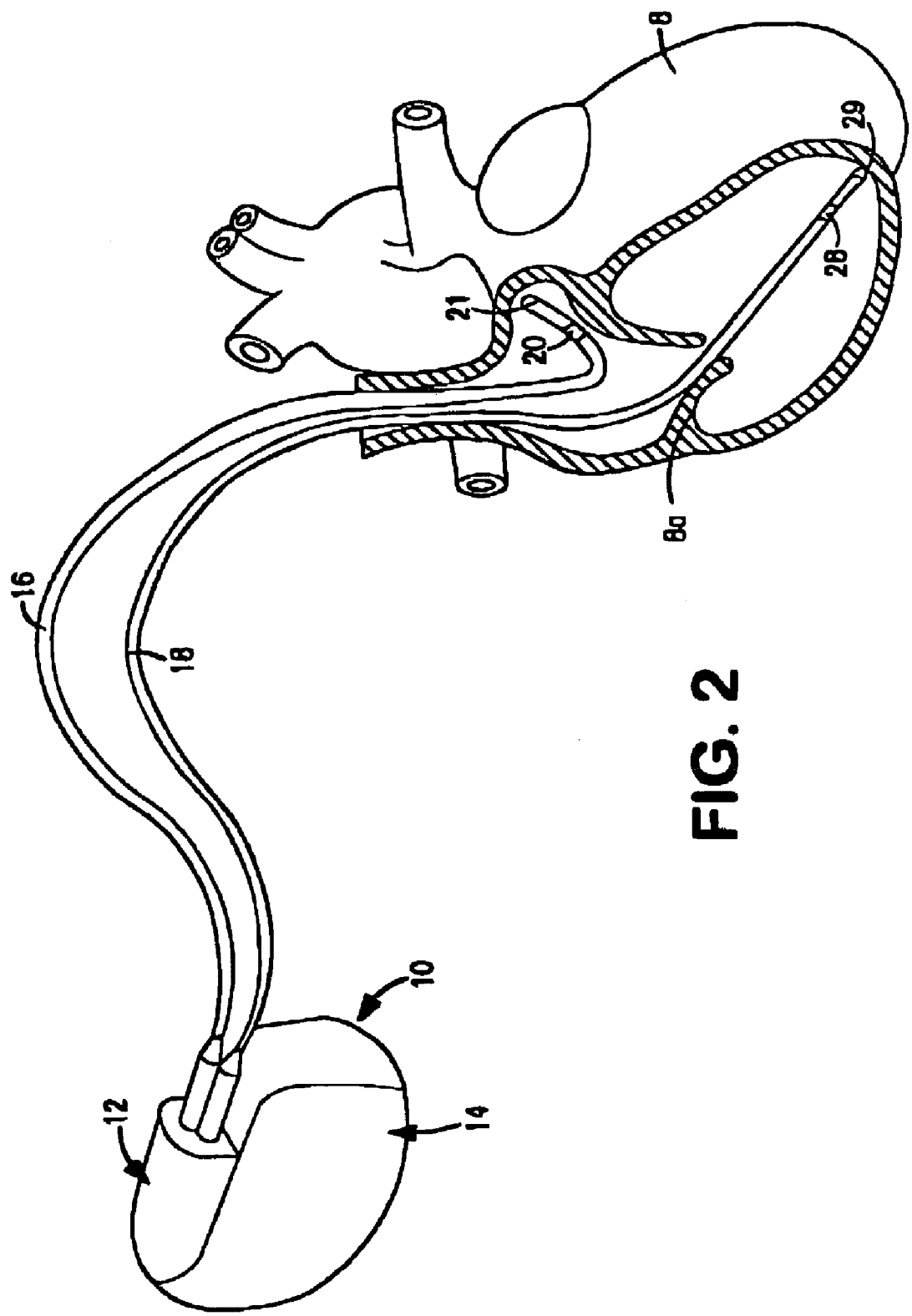
FIG. 2 is an enlarged view of the IMD of FIG. 1 diagrammatically illustrating coupling with the patient's heart in accordance with one embodiment of the invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
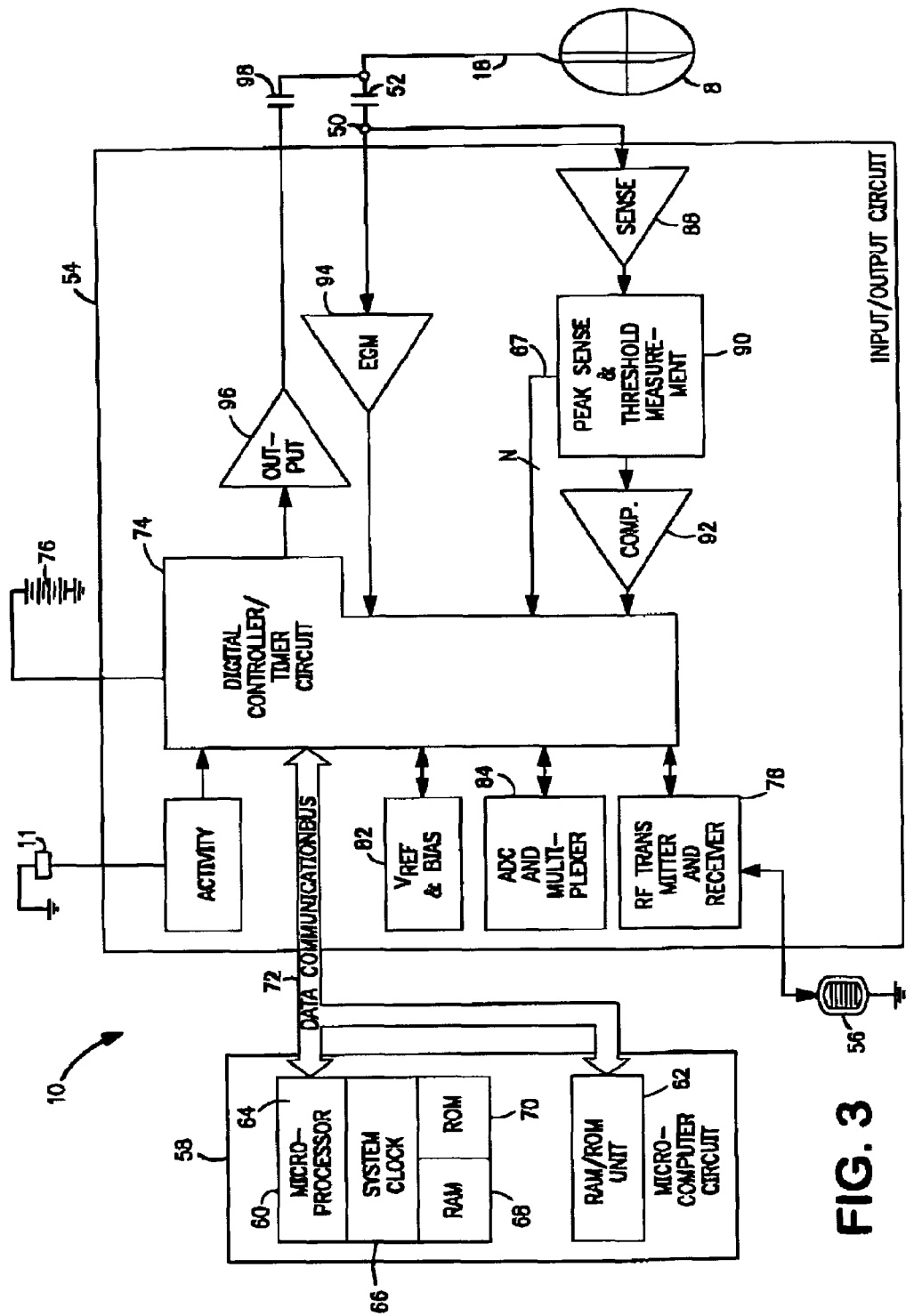
FIG. 3 is a functional block diagram of an IMD in accordance with one embodiment of the present invention where the IMD is a pacemaker.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple- chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
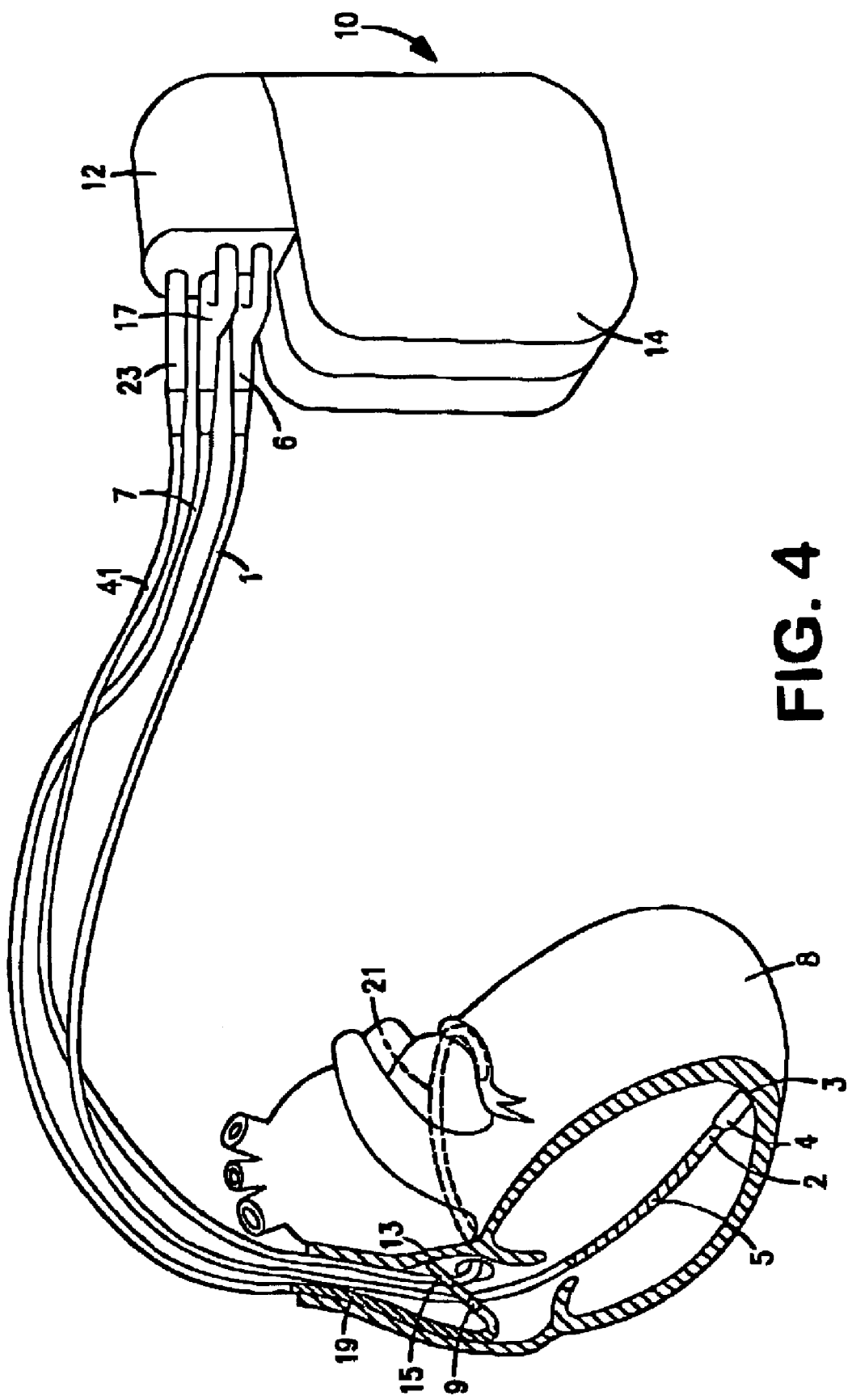
FIG. 4 is an IMD in accordance with another embodiment of the invention, wherein the IMD is an implantable pacemaker-cardioverter-defibrillator (PCD)
Figure 5:
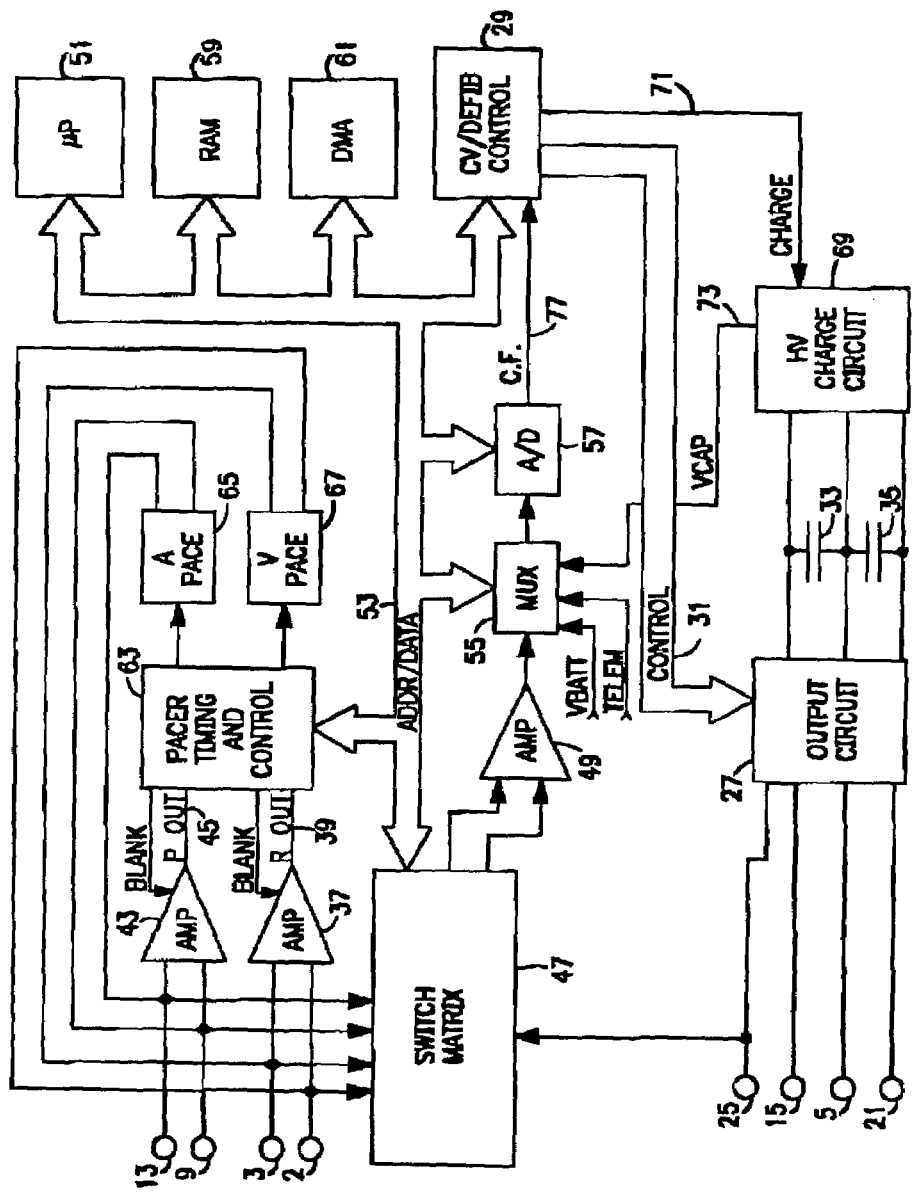
FIG. 5 is a functional block diagram of the IMD of FIG. 4.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Various embodiments of IMD 10 are described above. Attention is now directed to ultrasound apparatus and methods using same that, in general, may be used to determine fluid flow velocity (e.g., blood flow velocity), or, as further described below, may be implemented with an IMD for use in detecting various physiological events, e.g., ventricular tachycardia, and/or for supplementing the delivery of pacing therapy, or for measuring other types of motion, e.g., tissue movement of blood vessel walls, the brain, or muscle tissue.

Figure 6:
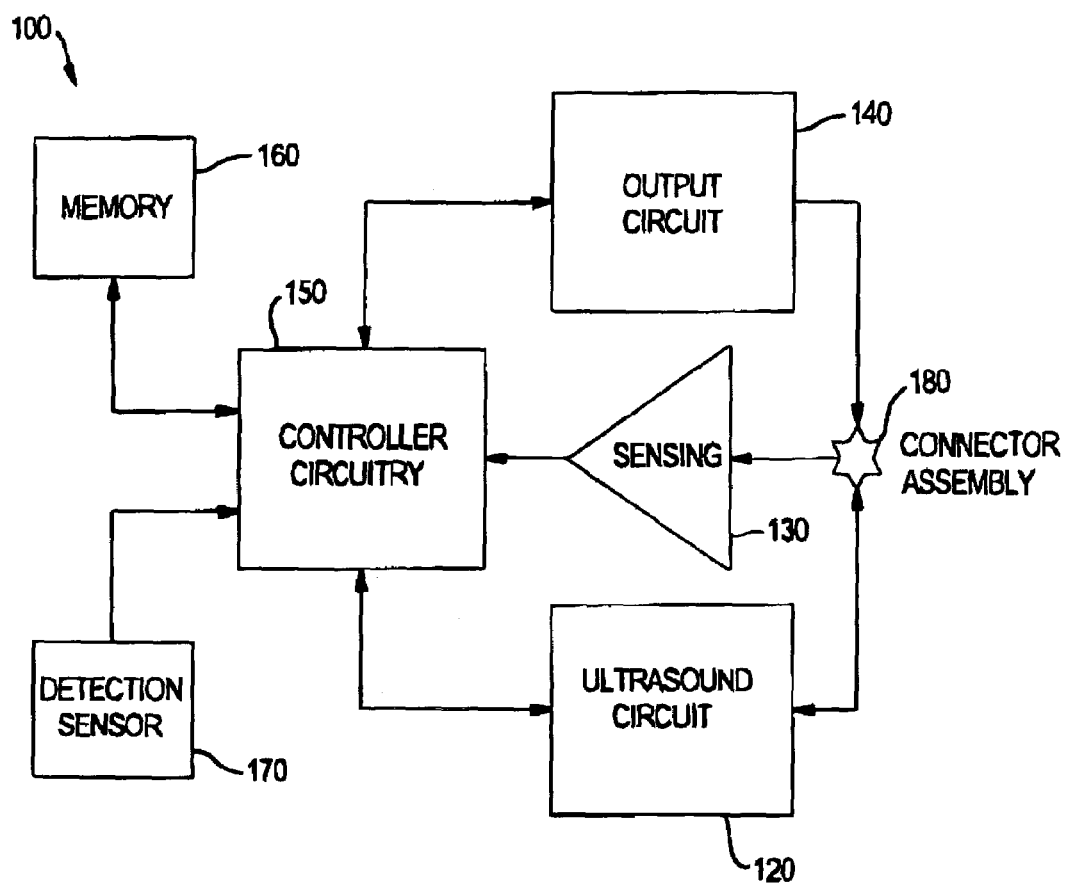
FIG. 6 is a generalized block diagram of an IMD that includes an ultrasound circuit in accordance with one embodiment of the present invention.

FIG. 6 is a simplified block diagram illustrating an exemplary embodiment of an IMD 100. For example, the IMD may be capable of treating tachyarrhythmia and delivering single lead VDD pacing as well as rate responsive pacing similar to IMD 10 described above. IMD 100 is in many aspects similar to IMD 10. IMD 100 includes controller circuitry 150, sensing circuit 130, and output circuit 140. IMD 100 further includes an ultrasound circuit 120. The ultrasound circuit 120 is in communication with controller circuitry 150 and also in communication with connector assembly 180.

It will be recognized that the ultrasound circuitry, i.e., Doppler circuitry, may be incorporated into any of various IMDs, such as those described elsewhere herein. Further, ultrasound methods described herein may be used in combination with any ultrasound IMDs and further may be used in any other medical devices, e.g., where battery power is to be conserved, such as portable devices.

Examples of ultrasound circuit 120 include those disclosed in U.S. Pat. No. 5,243,976 to Ferek-Petric et al. In general, Doppler circuit 120 detects and measures the blood flow, and an analog-to-digital converter circuit (e.g., analog-to-digital circuit 57 of FIG. 5) prepares the envelope of the Doppler waveform for digital processing. The Doppler circuit 120 is preferably designed to operate in the PW mode as opposed to CW mode. The PW mode uses a single transducer for transmission and reception, whereas the CW mode requires two transducers. The use of a single transducer may be advantageous when the transducer is mounted onto a catheter that may have limited surface area. Further, PW modes have flexible ranging capabilities that allow adjustment of a range gate at implantation, unlike the CW mode which may not have range gates that are adjustable. Blood flow can be measured at characteristic phases of the cardiac cycle, e.g., in diastole, thereby saving energy from the pacemaker power source. Data collected in this way can be fed into an IMD processor and used for controlling the pacemaker.

Figure 10:
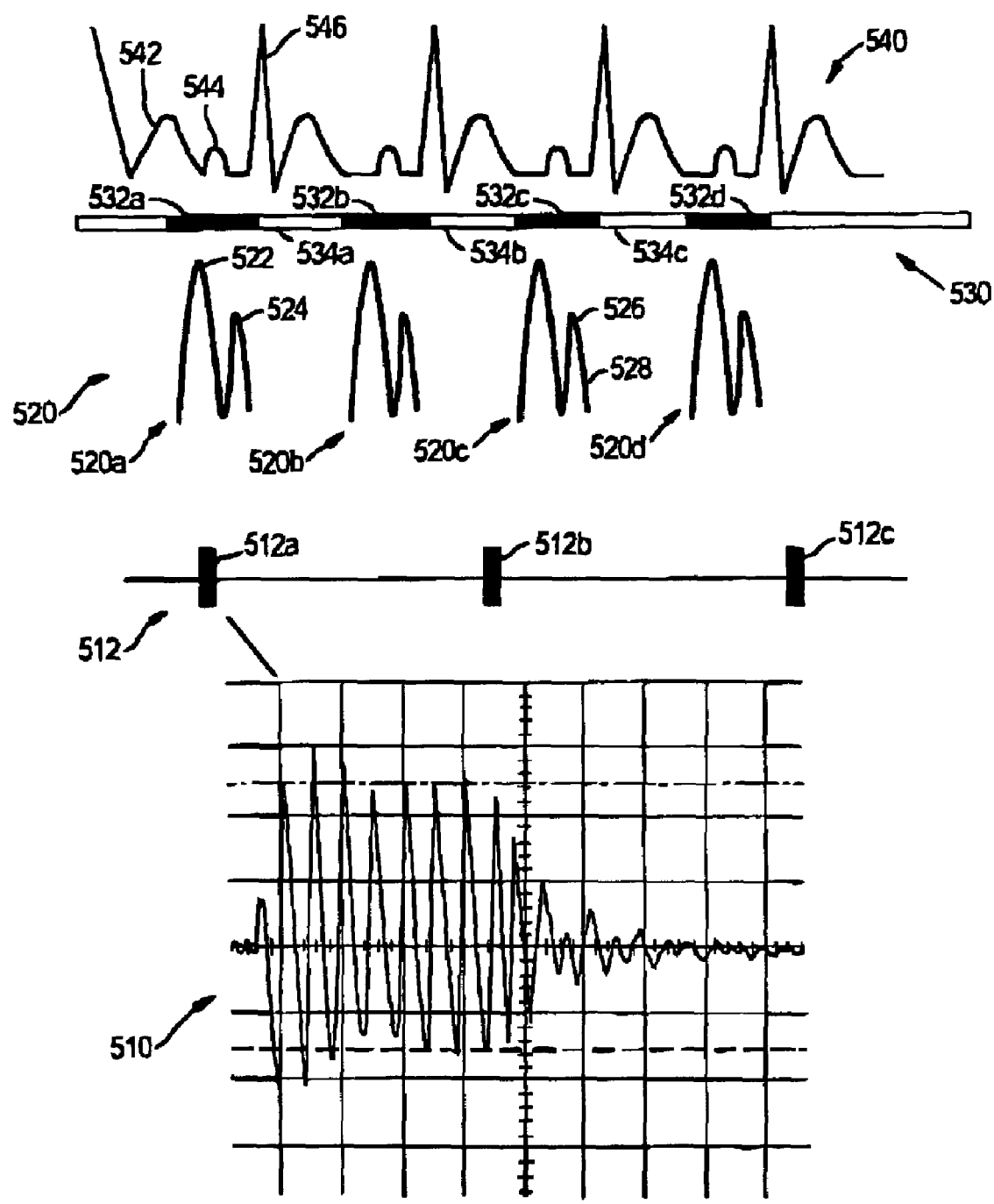
FIG. 10 is a graph illustrating the ultrasound method of FIG. 9 in relation to a plurality of cardiac cycles.

In the PW mode, the ultrasound circuit 120 is operable to provide pulsed Doppler signal packages as depicted and described in, for example, FIG. 10. As illustrated in FIG. 10, a Doppler transducer (not shown) emits several pulsed Doppler signal packages 512. Each package contains several periods of vibrations of the Doppler transducer. For example, pulsed Doppler signal package 510 includes nine periods of vibration. Each pulsed Doppler signal package is reflected by matter contained within a portion of blood as it flows, in this case, through the tricuspid valve. After being reflected, the pulsed Doppler signal package returns to the Doppler transducer having a slightly different frequency of vibration than when it was originally transmitted. By using Doppler methods well known in the art, the velocity of the portion of blood that was measured can be determined by the frequency shift between the transmitted pulsed Doppler signal package and the reflected pulsed Doppler signal package.

Ultrasound circuit 120 is in communication with an implantable lead (not shown) via connector assembly 180. For example, the implantable lead may include any ultrasonic transducer capable of transmitting and receiving pulsed Doppler signal packages. In general, such a lead may include a pulsed wave flow measurement piezoelectric transducer. Any suitable implantable lead capable of delivering pulsed Doppler signal packages known in the art may be used with the embodiments of the present invention. For example, the implantable leads described in U.S. Pat. No. 5,243,976 may be used to deliver pulsed Doppler signal packages to a region proximate a tricuspid valve of a heart. Also as shown therein, a pulsed wave flow measurement cardiac piezoelectric transducer used in combination with pacing leads and electrodes known in the art may also be used with the embodiments of the present invention.

The sensing circuit 130 of IMD 100 provides for sensing of intracardiac electrograms. Such electrograms may be utilized for analysis and tachycardia detection. The generalized output circuit 140 provides for delivery of therapy/pacing and/or high voltage paces as is known in the art. The sensing circuitry and output circuit depends on the IMD being employed. Various functionality for such circuits has been described elsewhere herein.

Controller circuitry 150 of IMD 100 may include, or be associated with, memory 160. Detection sensor 170 (e.g., rate responsive sensor) may include any suitable sensor for detecting a required physiological parameter, e.g., an accelerometer on a chip as described herein, a heart rate sensor, etc. Sensor 170 output as described herein may be used to turn on and off the ultrasound circuitry.

Ultrasound circuits in accordance with the present invention may be used to measure the velocity of any type of fluid flow, e.g., fluid flow in a pipe, pressurized line, hydraulic systems, etc. Preferably, however, ultrasound circuits according to the present invention are used in connection with an IMD to determine blood flow velocity. The measurement of fluid flow velocity as it generally applies to any fluid will first be described in reference to FIGS. 7–8. Thereafter, methods and apparatus for measuring blood flow velocity in relation to IMDs and the cardiac cycle will be described with reference to FIGS. 9–19. It will be understood by those skilled in the art that the methods and apparatus described in relation to the cardiac cycle may also be used to measure fluid flow velocity in a non-physiologic system, in an external medical device as opposed to an IMD, etc.

Figure 7:
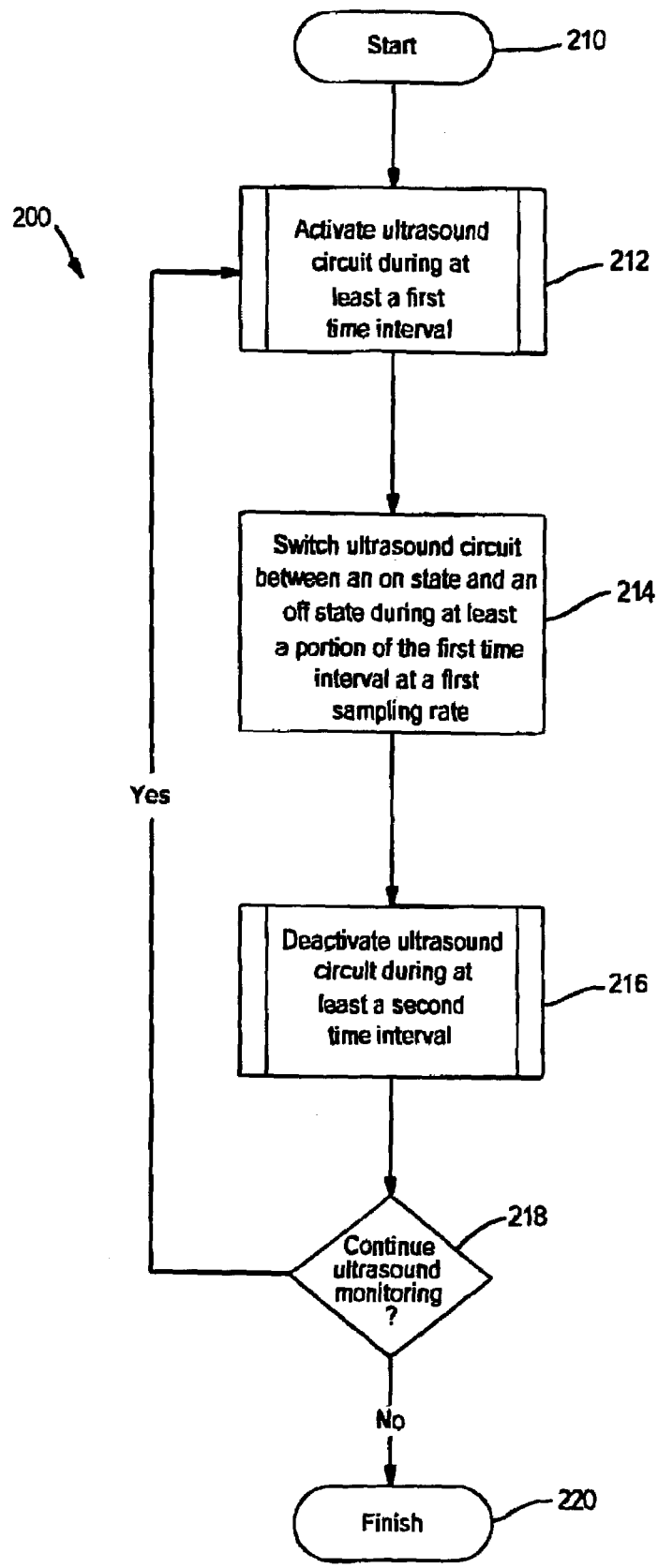
FIG. 7 is a flow diagram illustrating a dual sampling ultrasound method having a first sampling rate in accordance with one embodiment of the present invention.

FIG. 7 is a flow diagram illustrating an exemplary dual sampling method 200 for use with an ultrasound circuit in measuring fluid flow velocity in accordance with one embodiment of the invention. Upon start (block 210) of the method, the controller circuitry at 212 (e.g., controller circuitry 150 of FIG. 6) activates the ultrasound circuit (e.g., ultrasound circuit 120 of FIG. 6) during at least a first time interval. When activated, the controller circuitry at 214 switches the ultrasound circuit between an on state, where pulsed Doppler signal packages are provided, and an off state, where pulsed Doppler signal packages are not provided. The controller circuitry is operable to switch the ultrasound circuit between the on state and the off state at a first rate. When in the on state, the ultrasound circuit provides pulsed Doppler packages such that fluid flow velocity may be determined using Doppler techniques known in the art. The controller circuitry may switch the ultrasound circuit between the on state and the off state (i.e., samples flow velocity) during the entire time interval that the ultrasound circuit is activated or only a portion of the time interval. By being switched between the on state and the off state at the first rate, the ultrasound circuit conserves battery power by sampling fluid flow velocity only during the on state.

At 216, the controller circuitry deactivates the ultrasound circuit during at least a second time interval. Once deactivated, the ultrasound circuit is no longer capable of being switched between the on state and the off state. Therefore, pulsed Doppler signal packages are not provided when the ultrasound circuit is deactivated. At 218, the ultrasound monitoring may either be continued at 212 or discontinued at 220.

Figure 8:
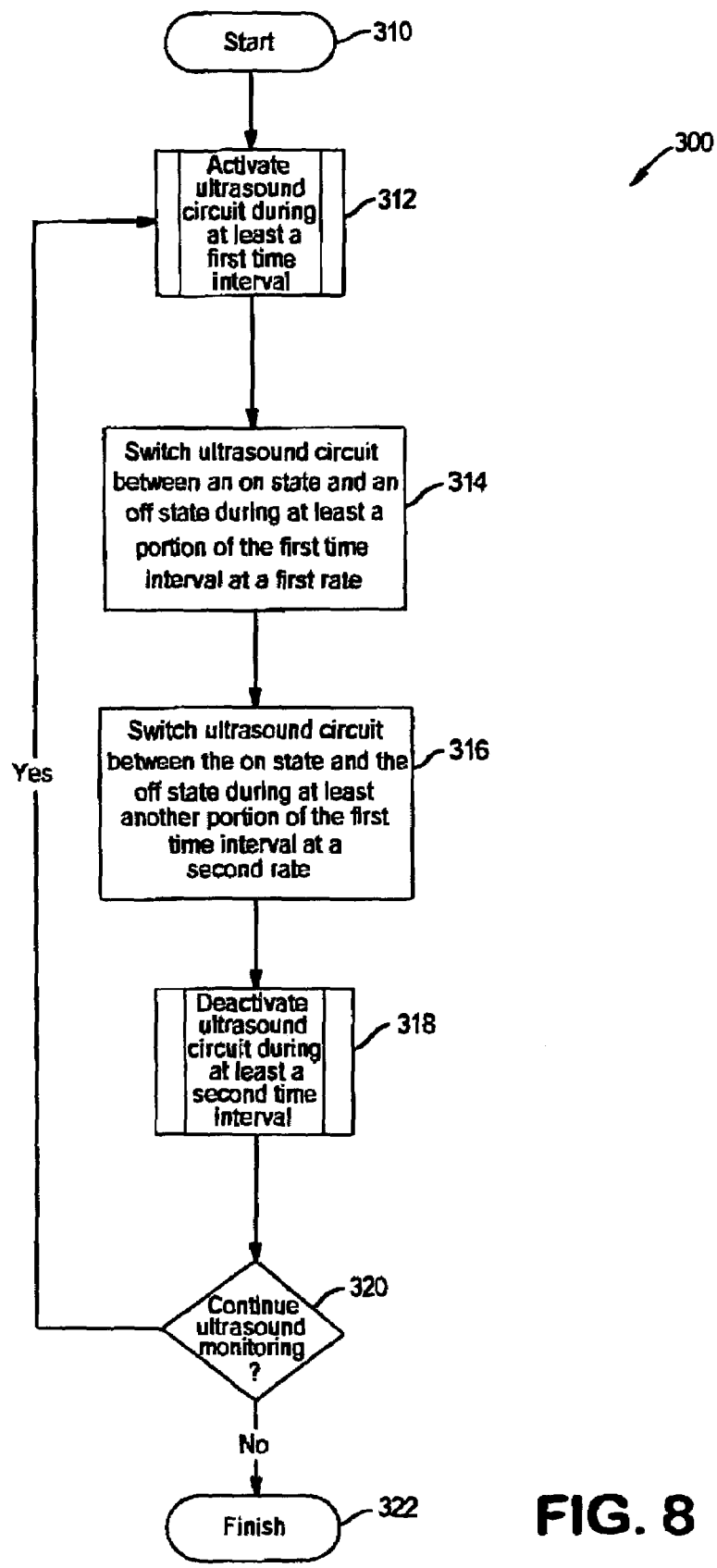
FIG. 8 is a flow diagram illustrating a dual sampling ultrasound method having a first sampling rate and a second sampling rate in accordance with another embodiment of the present invention.

FIG. 8 is a flow diagram illustrating an exemplary dual sampling ultrasound method 300 having a first sampling rate and a second sampling rate for use with an ultrasound circuit in measuring fluid flow velocity in accordance with another embodiment of the invention. Method 300 is similar in many respects to method 200 as described above. Upon start (block 310) of the method 300, the ultrasound circuit is activated during at least a first time interval (block 312). After activation, the ultrasound circuit at 314 is switched between an on state and an off state during at least a portion of the first time interval at a first sampling rate. At 316, the ultrasound circuit is switched between the on state and the off state during at least another portion of the first time interval at a second sampling rate. Following the sampling, the ultrasound circuit is deactivated at 318 and a determination is made at 320 whether to continue ultrasound monitoring.

Among the differences between method 300 and method 200 is that at 316 the controller circuitry switches the ultrasound circuit between the on state and the off state during at least another portion of the first time interval at the second sampling rate. The second sampling rate is different from the first rate. One skilled in the art will recognize that the ultrasound circuit may be switched between the on state and the off state at the first sampling rate during one or more time intervals, while the ultrasound circuit may also be switched between the on state and the off state at the second sampling rate during one or more different time intervals.

Although depicted as having two different sampling rates, the methods of the present invention are operable to sample fluid flow velocity at any number of different sampling rates. Further, the controller circuitry of the present invention is also operable to change sampling rates based on detection of various rate switching events as will be described in more detail herein.

Although sampling fluid flow velocity as generally described may also incorporate the methods described below, for simplicity and clarity, the remaining embodiments of the present invention will be described in reference to the use of ultrasound circuits for measuring blood flow velocity, e.g., such as employed for use with cardiac therapies.

Figure 9:
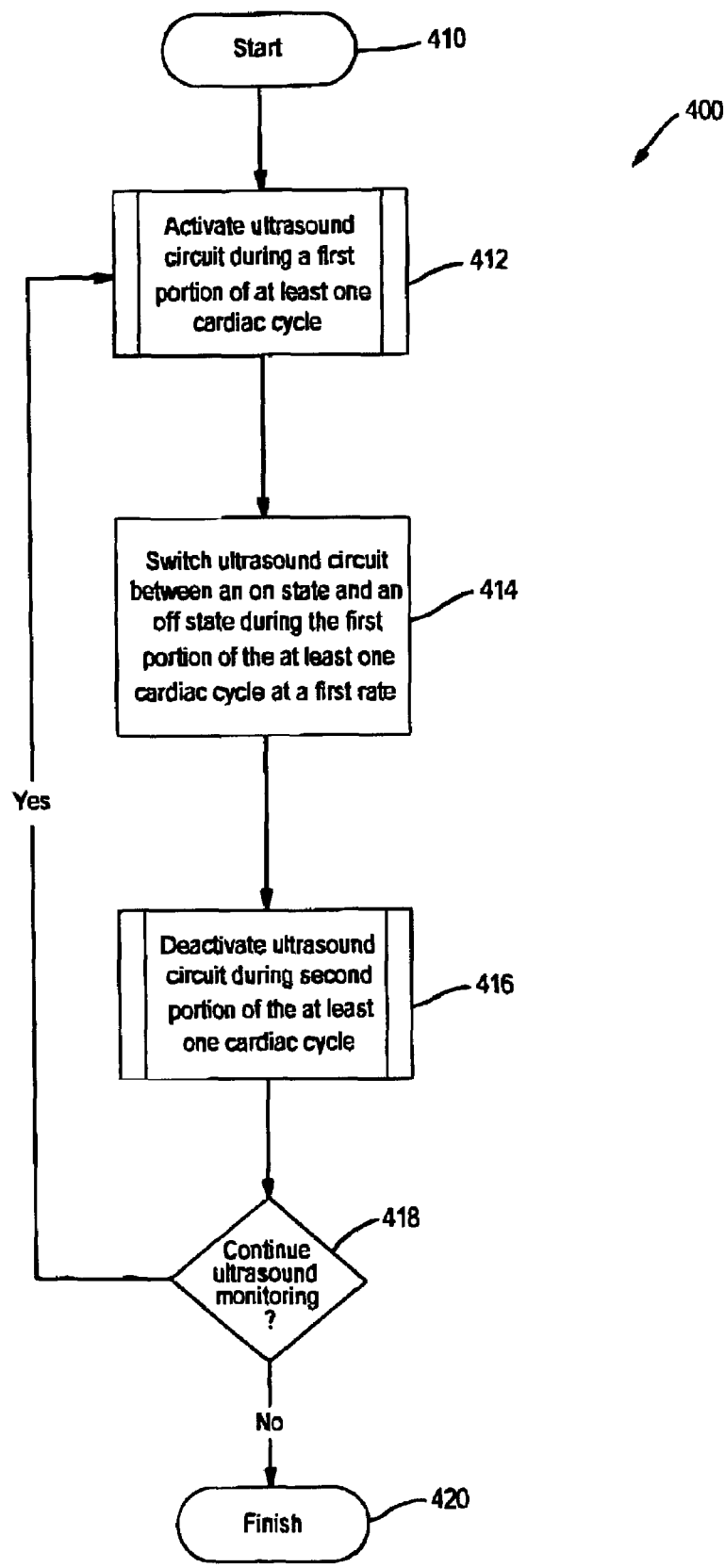
FIG. 9 is a flow diagram illustrating a dual sampling ultrasound method in relation to at least one cardiac cycle in accordance with another embodiment of the present invention.

FIG. 9 is a flow diagram illustrating a dual sampling ultrasound method in relation to at least one cardiac cycle in accordance with another embodiment of the present invention. Upon the start at block 410, controller circuitry (e.g., controller circuitry 150 of FIG. 6) at 412 activates an ultrasound circuit (e.g., ultrasound circuit 120 of FIG. 6) during a first portion of at least one cardiac cycle. The cardiac cycle may be sensed using sensing circuitry known in the art, e.g., sensing circuitry 130 in FIG. 5, such as that for recording an electrocardiogram. After activating the ultrasound circuit, the controller circuitry at 414 switches the ultrasound circuit between an on state, where pulsed Doppler signal packages are provided, and an off state, where pulsed Doppler signal packages are not provided, during the first portion of the at least one cardiac cycle at a first rate.

At 416, the controller circuitry deactivates the ultrasound circuit during a second portion of the at least one cardiac cycle such that pulsed Doppler signal packages are not provided during the second portion of the at least one cardiac cycle. At 418, ultrasound monitoring may be continued by returning to 412 during subsequent cardiac cycles, or the method may be terminated at 420.

As illustrated in FIG. 9, dual sampling method 400 is used to conserve battery power. First, pulsed Doppler signal packages are only sent during the DMI (e.g., when the ultrasound circuit is activated at 412). Pulsed Doppler signal packages are not sent during the DRP (e.g., when the ultrasound circuit is deactivated at 416). Second, during the DMI, the ultrasound circuit is switched on and off (e.g., at 414).

An alternative manner of describing method 400 may include sampling blood flow velocity at a first sampling rate at 414. As used infra, blood flow velocity sampling may be achieved by switching the ultrasound circuit between the on state and the off state at a sampling rate. For example, sampling blood flow velocity at a first sampling rate is achieved by switching the ultrasound circuit between the on state and the off state at the first sampling rate during the DMI, the first sampling rate being the number of times the ultrasound circuit is switched per unit time. During the DRP, the blood flow velocity is not sampled.

Although method 400 depicts the controller circuitry as activating and deactivating the ultrasound circuit during the same cardiac cycle, the controller circuitry is further operable to activate the ultrasound circuit during one cardiac cycle and deactivate the ultrasound circuit during the next cardiac cycle or maintain the activation of the ultrasound circuit during several consecutive cardiac cycles followed by deactivation for several subsequent cycles.

FIG. 10 corresponds to and illustrates one exemplary embodiment of the ultrasound method 400 described above and illustrated in FIG. 9. FIG. 10 corresponds to measuring blood flow velocity at a region proximate a tricuspid valve of a heart (see, e.g., tricuspid valve 8a of FIG. 2). Although blood flow velocity may be sampled proximate other regions of the heart, e.g., pulmonary vein, vena cava superior or coronary sinus, sampling blood flow velocity proximate the tricuspid valve is preferred because it does not require special implantation procedures and gives an abundance of data for therapy control, disease follow-up, and patient diagnostics. Further, sampling blood flow velocity proximate the tricuspid valve is preferred because the velocity waveforms at the tricuspid valve exhibit two distinct waves when the heart is functioning normally, while the relationship and/or existence measurably changes for certain pathological conditions.

FIG. 10 includes pulsed Doppler signal packages 512a–c, each of which resemble pulsed Doppler signal package 510. FIG. 10 further includes tricuspid blood flow velocity waveforms 520a–d (i.e., 520), electrocardiogram 540, and ultrasound circuit activation bar 530.

In the embodiment illustrated in FIG. 10, electrocardiogram 540 includes P waves 544, QRS complexes 546, and T waves 542 illustrating a normal electrocardiogram 540. Ultrasound circuit activation bar 530 includes Doppler refractory period 534 (DRP) and Doppler measurement interval 532 (DMI). The DRP 534 begins at the onset of the QRS complex 546, while the DMI begins following completion of the T wave 542.

In general, after the repolarization of the heart that caused T wave 542, the relaxation of the heart muscle causes the early diastolic filling wave 522 having peak blood velocity E (hereinafter "E-wave"). The following atrial depolarization causes the P wave 544 and corresponding atrial muscle contraction that pumps additional blood quantity producing the blood flow wave 524 having a peak velocity A (hereinafter "A-wave"). The ratio of peak velocities E/A is a hemodynamic parameter showing the cardiac muscle performance. The same Doppler waveform may be obtained when measuring the mitral valve flow where peak velocities have greater values (in order of 1 m/s), in comparison to tricuspid valve velocities that are half as fast.

To measure blood flow velocity, a Doppler ultrasound transmitter of the ultrasound circuit excites an ultrasonic transducer by a pulsed Doppler signal package 510. The pulsed Doppler signal package 510, for example, may include 9 periods of sinusoidal signal. The pulsed Doppler signal package 510 is repeated as packages 512a, 512b, and 512c at a sufficiently high frequency in order to record the Doppler frequency shift. As described further below, the frequency of the pulsed Doppler signal packages can be tuned to the maximum blood flow velocity. In this embodiment, the frequency of the provided pulsed Doppler signal packages 512 is approximately 20 kHz for measurement of a maximum blood flow velocity of 0.75 m/s during operation at 20 MHz and at a zero angle between the ultrasound beam and fluid flow.

Use of pulsed Doppler signal packages, as opposed to continuous wave Doppler techniques, decreases the power consumed by the ultrasound methods. In order to further decrease the power consumption, the ultrasound circuit is activated only during a portion of the cardiac cycle. For example, during DMI 532a, the ultrasound circuit is activated by controller circuitry (see 412 of FIG. 9). When activated, the ultrasound circuit is switched between the on state, represented by black segments 526 of waveform 520, and the off state, represented by gray segments 528 (see 414 of FIG. 9). Subsequently, during DRP 534*a*, the controller circuitry deactivates the ultrasound circuit (corresponding to 416 of FIG. 9). Although depicted as occurring for four cardiac cycles, the sampling continues for as many cycles as may be required or desired.

Blood flow velocity waveform 520 illustrates the waveform sampling in a non-real timing relation whereby black waveform segments 526 are sampled waveform while gray segments 528 are non-sampled segments. Each black waveform segment 526 represents a plurality of pulsed Doppler signal packages 512. In other words, blood flow velocity waveform 520 is sampled at a first sampling rate where the ultrasound circuit is switched between the on state and the off state at the first sampling rate, which is represented by black waveform segments 526. While in the on state, the ultrasound circuit provides a plurality of pulsed Doppler signal packages 512.

According to the Nyquist sampling theorem, the blood flow velocity has to be sampled at a sampling rate that is at least double the upper frequency limit of the blood flow velocity Doppler shift. Preferably, in this illustrated embodiment, the sampling frequency has to be at least 200 Hz.

Accordingly, the present invention provides a dual sampling system whereby aliasing of the blood flow velocity waveform 520 may be prevented and the maximum flow velocity (e.g., E and A) may be recorded.

From the sampled segments, a tricuspid blood flow velocity waveform (i.e., waveform 520) may be interpolated using circuitry and programming that are well known in the art.

Figure 11:
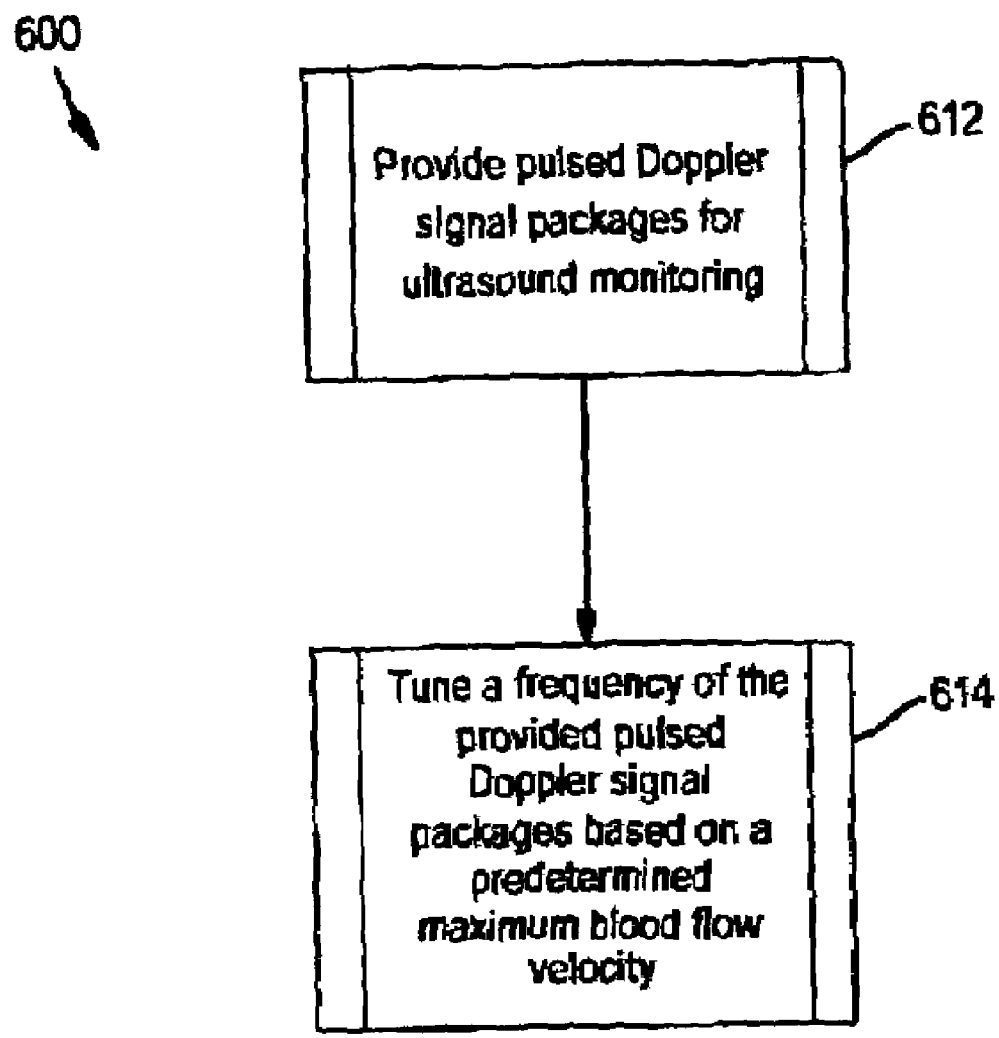
FIG. 11 is a flow diagram illustrating a dual sampling ultrasound method that is tunable to a predetermined maximum blood flow velocity in accordance with another embodiment of the present invention.

FIG. 11 is a flow diagram illustrating a dual sampling ultrasound method that is tunable to a predetermined maximum blood flow velocity in accordance with another embodiment of the present invention. The method 600 is preferably used with one or more of the other methods, e.g., dual sampling method 400, described herein. At 612, blood flow velocity is measured using the provision of pulsed Doppler signal packages in accordance with the methods described above and/or any other pulsed Doppler devices or processes. At 614, the frequency that pulsed Doppler signal packages are provided is tuned based on a predetermined maximum blood flow velocity that is to be measured. Such tuning may occur before or after the pulsed Doppler process has been activated.

For example, with reference to FIG. 10, the frequency that pulsed Doppler signal packages 512 are provided during the on state of the ultrasound circuit may be set based on the maximum blood flow velocity that is to be measured as well as an angle between the ultrasound beam and the blood flow. By presetting this frequency, battery power may further be conserved through lowering the frequency of pulsed Doppler signal packages for patients having lower maximum blood flow velocities. The conservation of battery power can provide IMDs with a longer lifespan.

Additional energy savings may be achieved by minimization of a range that the pulsed Doppler signal packages are projected and pulse length of the pulsed Doppler signal packages. Reduction of the measurement range and pulse length reduces the total energy consumption. However this must be done in a controlled way as not to measure within the flow boundary layer. One skilled in the art can, at the time of implantation and first programming adjust these parameters to obtain good measurement results at minimum range and pulse length.

Figure 12:
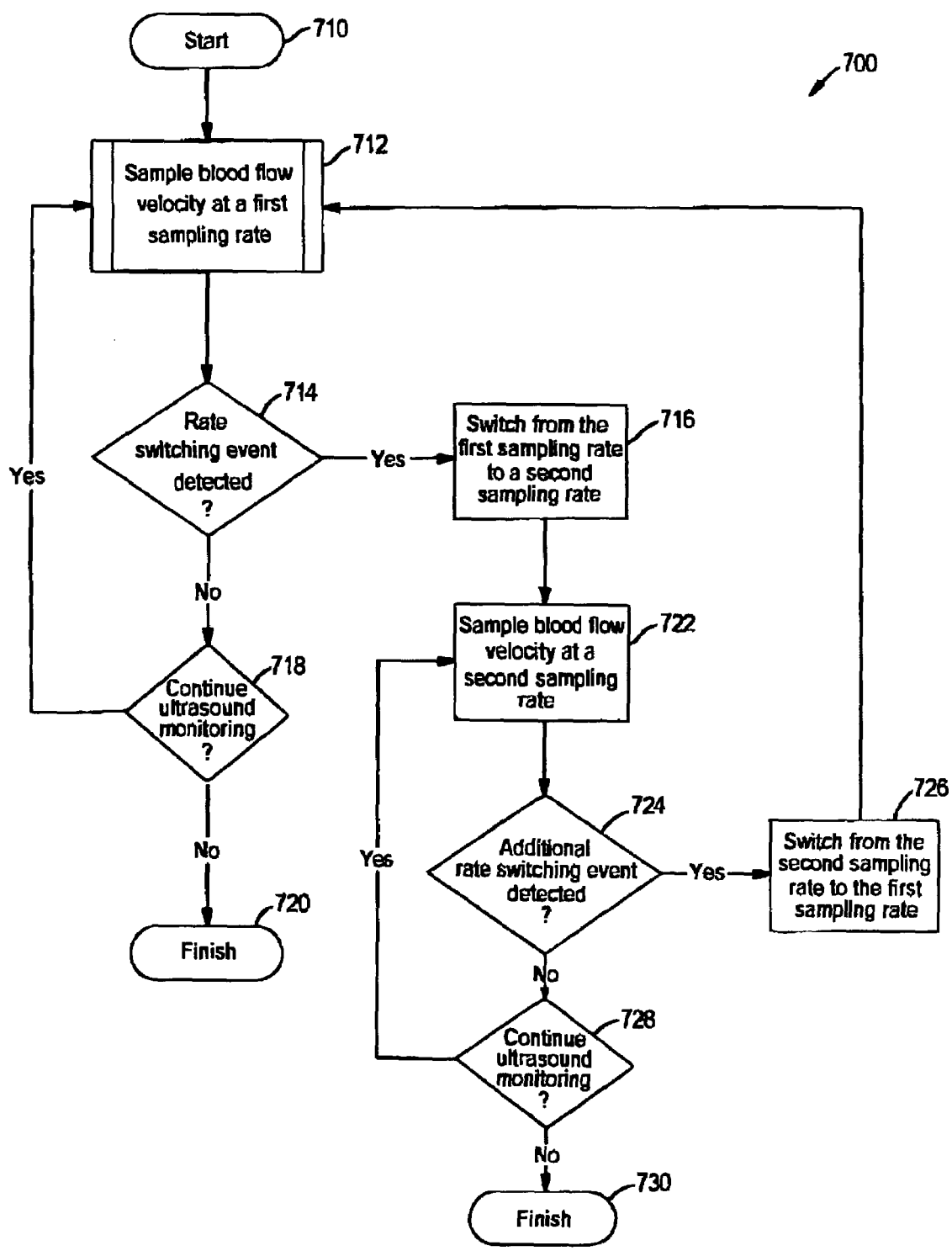
FIG. 12 is a flow diagram illustrating a dual sampling ultrasound method in relation to a rate switching event in accordance with another embodiment of the present invention.

As described above, the IMDs of the present invention are capable of sampling blood flow velocity at several different sampling rates (e.g., the multiple sampling rates shown in FIG. 8), and/or using one or more different methods (e.g., the methods described with reference to FIGS. 7–9 and 11). FIG. 12 is a flow diagram illustrating a dual sampling ultrasound method in relation to a rate switching event in accordance with yet another embodiment of the present invention. Upon start at block 710 of the method 700, blood flow velocity is sampled at a first sampling rate at block 712 in accordance with the present invention as described above. For the first sampling rate, the ultrasound circuit is switched between an on state, where pulsed Doppler signal packages are provided, and an off state, wherein pulsed Doppler signal packages are not provided, over at least a first period of time at the first sampling rate. For example, the first sampling rate may be used during a first portion of the cardiac cycle, e.g., DMI 532 of FIG. 10.

A detection sensor (e.g., detection sensor 170 of FIG. 6) or any other monitoring apparatus, determines whether a rate switching event has been detected at 714. Rate switching events may include increased/decreased patient activity, increased/decreased heart rate, or any other physiological parameter such as those known in the art that are used in conjunction with IMD delivered therapy. If a rate switching event is detected, the first sampling rate is switched to a second sampling rate at 716, e.g., under control of controller circuitry. If a rate switching event is not detected at 714, then the method determines whether ultrasound monitoring will continue by returning to 712, or discontinue at 720.

Once the controller circuitry switches from the first sampling rate to the second sampling rate at 716, blood flow velocity is sampled at the second sampling rate at 722. As described above, when the IMD is sampling blood flow velocity at the second sampling rate, the controller circuitry is switching the ultrasound circuit from the on state, where pulsed Doppler signal packages (e.g., 510 of FIG. 10) are provided, to the off state where pulsed Doppler signal packages are not provided, over at least a second period of time at the second sampling rate, e.g., during DMI 532 of FIG. 10.

At 724, it is determined whether an additional rate switching event has been detected. If the additional rate switching event is detected, then the controller circuitry switches from the second sampling rate back to the first sampling rate at 726 (or another sampling rate), and method 700 returns to sampling blood flow velocity at the first sampling rate at 712 (or the other sampling rate). If an additional rate switching event is not detected at 724, then method 700 determines whether to continue ultrasound monitoring at 728. If ultrasound monitoring is to continue, then method 700 returns to sampling blood flow velocity at the second sampling rate at 722. If monitoring is to be discontinued, then the method 700 is finished (block 730).

FIGS. 13*a–c* correspond to and illustrate different embodiments of the ultrasound method as described above and illustrated in FIG. 12. In FIG. 13*a*, tricuspid blood flow velocity is sampled at the first sampling rate (see 712 of FIG. 12) whereby the black segments 820 of the waveform 810 represent sampled segments and the gray segments 822 represent non-sampled segments. As illustrated in FIG. 13*a*, the entire tricuspid blood flow velocity wave for one cardiac cycle is sampled at the first sampling rate. FIG. 13*b* illustrates tricuspid blood flow velocity being sampled at the second sampling rate for one cardiac cycle. Being able to sample at multiple rates as illustrated in FIGS. 13*a–b* is useful in many situations to conserve battery power.

For example, there are many clinical utilities of the tricuspid flow waveform measurement. One of them is single lead VDD pacing, or A-wave synchronous ventricular pacing. In this mode of operation, only detection of the A-wave 814 is important while no specific measurements of the waveform parameters are needed because only the timing (i.e., occurrence) of the A-wave may be more important than its waveform morphology, e.g., maximum velocity, etc. As such, this detection mode can be performed with a relatively slow sampling rate as disclosed in FIG. 13*a*, when compared to the sampling rate necessary for rate responsive pacing where parameter measurements are necessary. For example, rate responsive pacing, on the other hand, requires measurement of the E-wave acceleration. Accordingly, a faster sampling rate (e.g., compared to the detection mode) is necessary to measure the first derivative of the E-wave 812. FIG. 13*b* illustrates the measurement mode sampling utilizing faster sampling rate than in detection mode. In other words, the sampled segments 830 (or non-sampled segments 832) occur much more frequently than segments 820 or 822.

FIG. 13*c* illustrates the tricuspid blood flow velocity being sampled at two different rates within a cardiac cycle. The E-wave 812 is sampled at the second sampling rate, and the A-wave 814 is sampled at the first sampling rate. Axis 840 illustrates the occurrence of a rate switching event (e.g., detection of rate switching event at 714 of FIG. 12). The detection of a rate switching event may occur within one cardiac cycle as illustrated in FIG. 13*c*, or the detection of the rate switching event may occur between each cardiac cycle, or after several cardiac cycles are sampled at the same rate.

The detection sensor or monitoring apparatus for detecting rate switching events (e.g., detection sensor 170 of FIG. 6) may be any suitable sensor apparatus known in the art for detecting any desired parameter, e.g., physiological parameter. For example, the detection sensor may include an accelerometer operable to detect patient activity.

Figure 14:
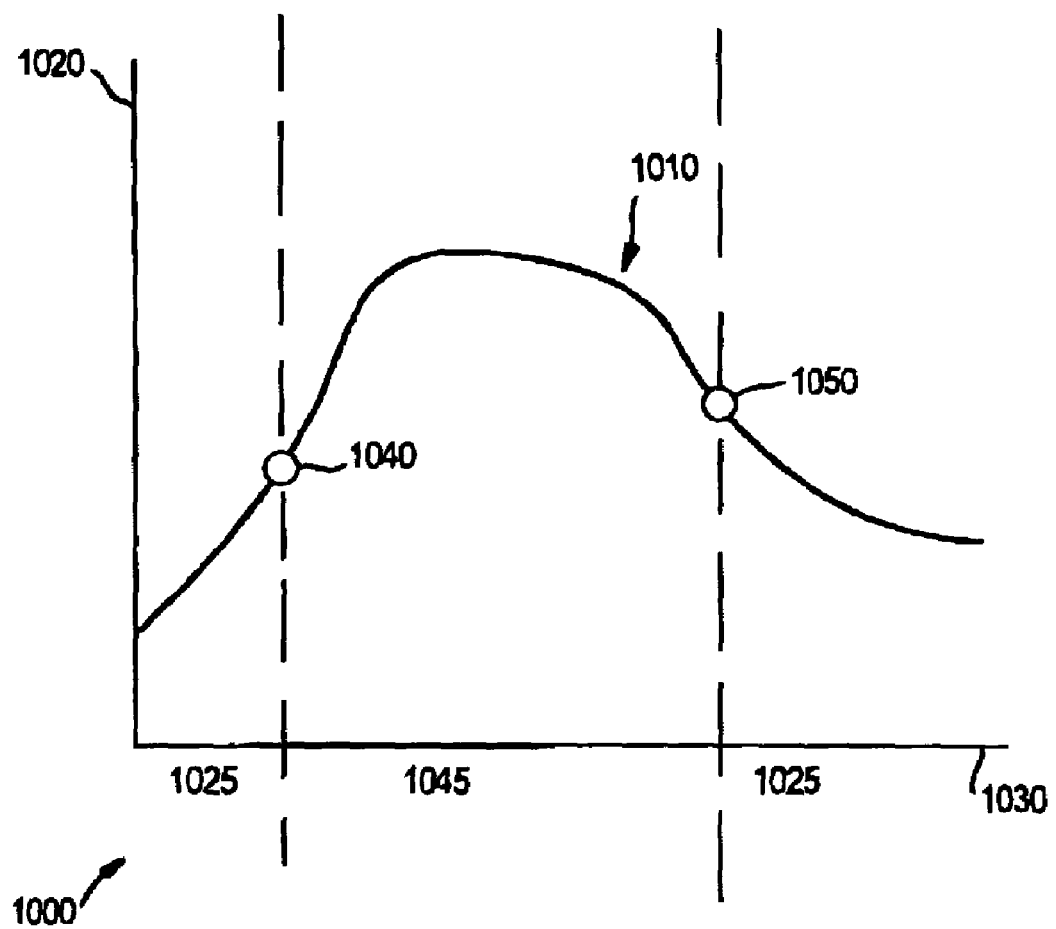
FIG. 14 is a graph illustrating an exemplary rate switching event in accordance with the dual sampling ultrasound method of FIG. 12.

As illustrated in an accelerometer curve 1000 of FIG. 14, which plots accelerometer signal amplitude 1020 (e.g., patient activity) versus time 1030, measurement mode sampling 1045 (i.e., the faster sampling rate illustrated in FIG. 13*b*) may be initiated by an accelerometer at time 1045. For example, in the case of physical exercise, an accelerometer signal 1010 increases and at a certain threshold, detection mode sampling 1025 is switched at 1040 to the measurement mode 1045 for sampling of the tricuspid blood flow velocity to measure the first derivative of the E-wave. When the accelerometer signal 1010 decreases its signal amplitude, the controller circuitry switches the ultrasound circuit back to detection mode 1025 at point 1050.

As described above, the ultrasound techniques described herein may be used in various IMDs. In one illustrative exemplary system, shown in FIG. 15, one or more of the ultrasound methods are used in IMDs for tachycardia detection and classification (e.g., IMD 10 of FIG. 5). In this embodiment, generally, the ultrasound circuit may be switched to the measurement mode upon detection of tachycardia by another criterion known in the art.

Figure 15:
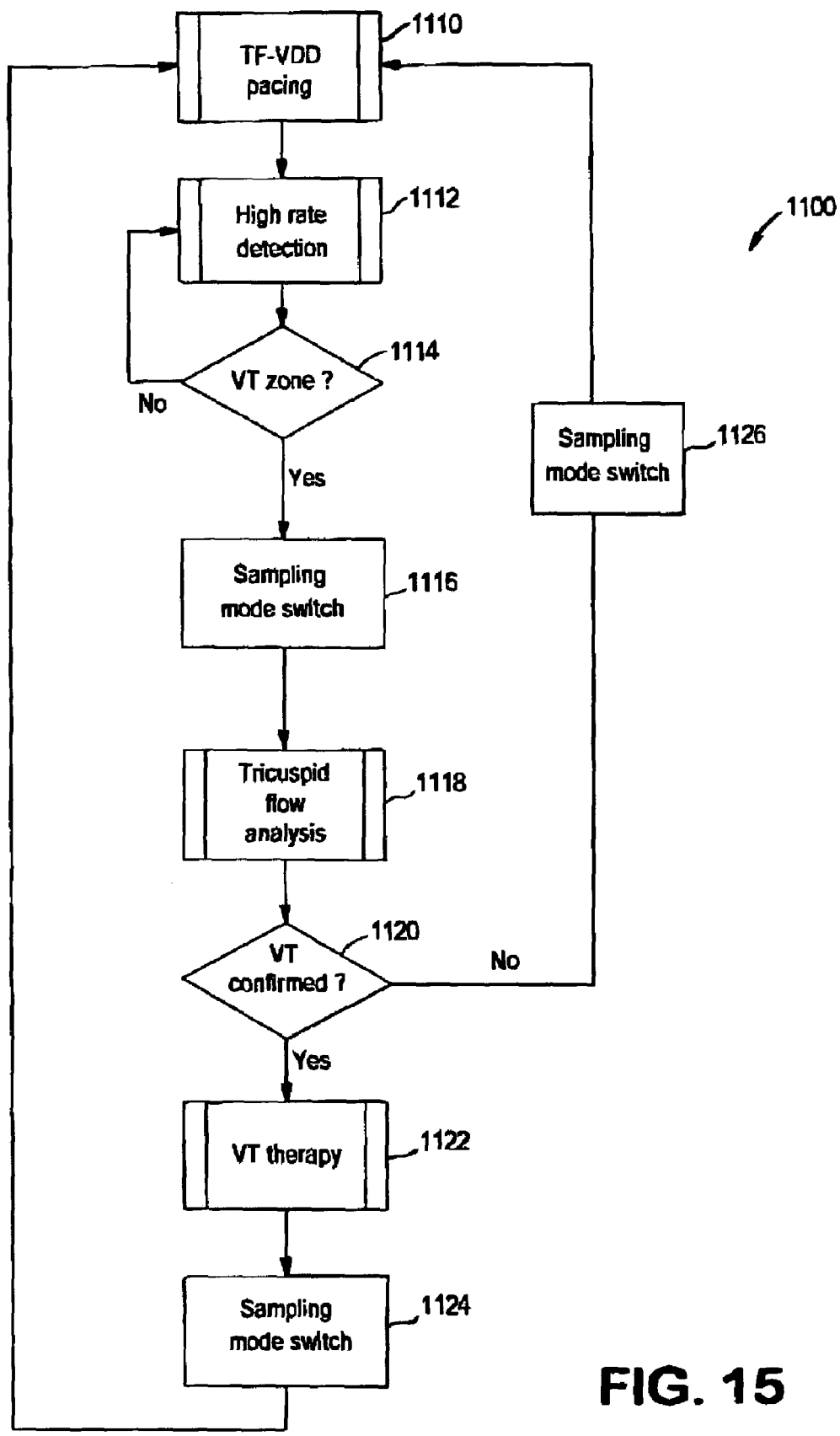
FIG. 15 is a flow diagram illustrating a dual sampling ultrasound method in relation to detection of ventricular tachycardia in accordance with another embodiment of the present invention.

As illustrated in FIG. 15, tricuspid flow VDD pacing (i.e., TF-VDD pacing) at 1110 is administered using an IMD as disclosed above. In a classical pacing system, a P-wave may trigger pacing. The TF-VDD pacing illustrated in FIG. 15, on the other hand, may be triggered by an A-wave.

While in TF-VDD pacing, the controller circuitry in this embodiment switches the ultrasound circuit between the on state and the off state at a first sampling rate (e.g., detection mode) as described above. Upon detection of a high heart rate using a detection sensor (e.g., detection sensor 170 of FIG. 6) at 1112, method 1100 determines whether the high rate is within a VT zone (e.g., a heart rate above a certain threshold for detecting ventricular tachycardia) at 1114 using methods known in the art. If the rate is within the VT zone, then at 1116 the controller circuitry switches the ultrasound circuit from the detection mode to the measurement mode in order to measure the blood flow velocity of the E-wave and calculate an acceleration (i.e., first derivative) of the E-wave (block 1118). If the acceleration of the E-wave is below a certain acceleration threshold, then VT is confirmed at 1120 and an appropriate VT therapy is delivered at 1122. If VT is not confirmed at 1120, then method 1100 returns to TF-VDD pacing at 1110 and the controller circuitry switches the ultrasound circuit back to detection mode. Once VT therapy has been completed at 1122, the controller circuitry switches the ultrasound circuit back to the detection mode at 1124.

The above illustrative example of the control of therapy using ultrasound techniques is only one of numerous therapies that can be employed. For example, various other therapies are described in U.S. Pat. No. 5,243,976 to Ferek-Petric et al. entitled "Tricuspid Flow Synchronized Cardiac Electrotherapy System with Blood Flow Measurement Transducer and Controlled Pacing Signals Based on Blood Flow Measurement," issued Sep. 14, 1993; U.S. Pat. No. 5,316,001 to Ferek-Petric et al. entitled "Cardiac Measurement System for Measuring Blood Flow Velocity by Use of a Sensor Implanted Inside the Heart," issued May 31, 1994; and U.S. Pat. No. 5,318,595 to Ferek-Petric et al. entitled "Pacing Method and System for Blood Flow Velocity Measurement and Regulation of Heart Stimulating Signals Based on Blood Flow Velocity," issued Jun. 7, 1994.

There are clinical applications of an IMD system where there is no interest in obtaining instantaneous blood flow velocity values, but rather the determination of average long-term blood flow velocity changes is required. In this case, sampling of the entire blood flow velocity waveform for each single cardiac cycle may be unnecessary and would use-up considerable battery power.

Figure 16:
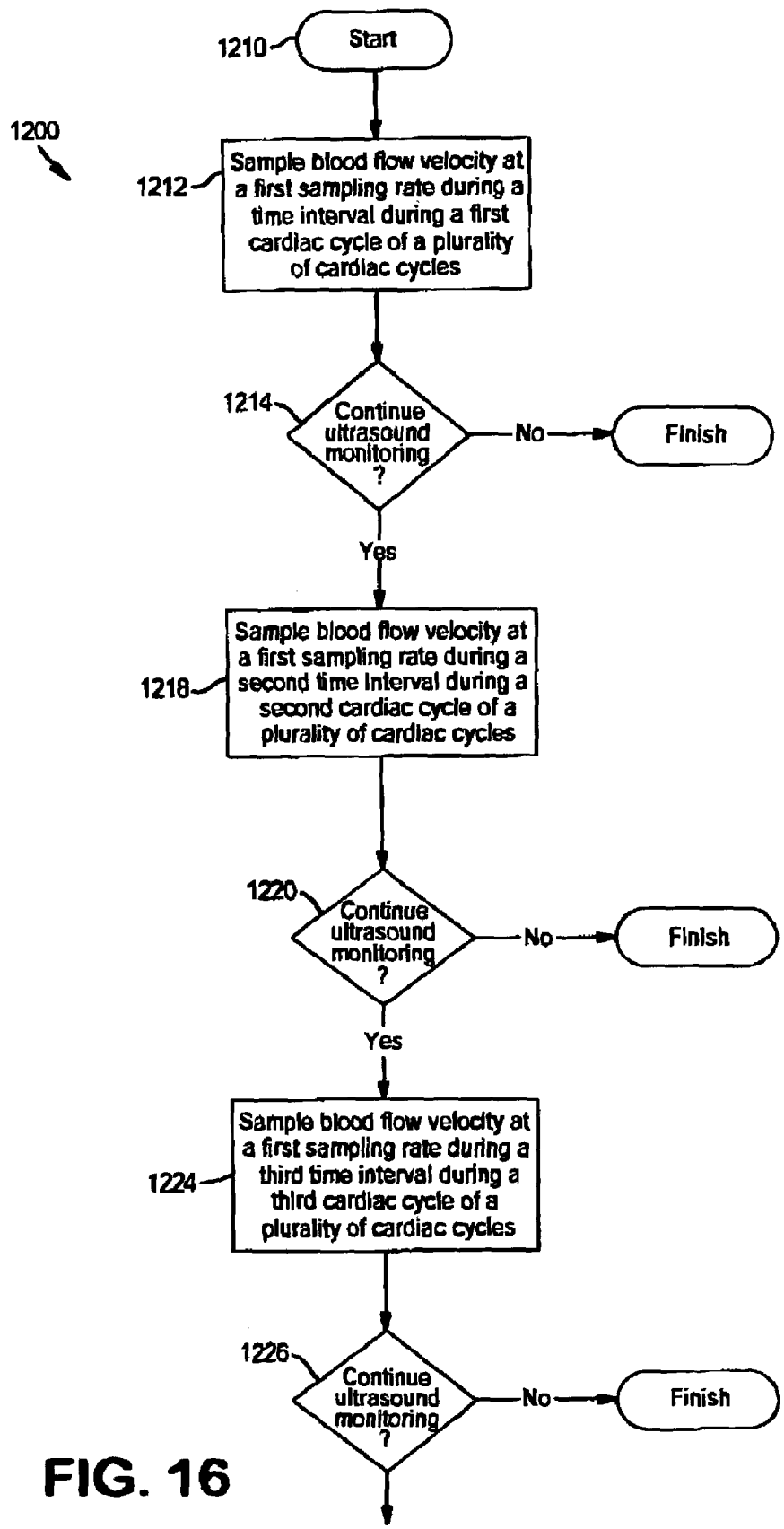
FIG. 16 is a flow diagram illustrating a dual sampling ultrasound method for determining an equivalent blood flow velocity waveform in accordance with another embodiment of the present invention.

FIG. 16 is a flow diagram illustrating a dual sampling ultrasound method for determining an equivalent blood flow velocity waveform in accordance with another embodiment of the present invention where average blood flow velocities over an extended period of time may be determined. Upon the start (block 1210) of the method 1200, blood flow velocity is sampled at a first sampling rate during a time interval during a first cardiac cycle of a plurality of cardiac cycles at block 1212. Sampling blood flow velocity at the first sampling rate may include any of the methods described above in accordance with the present invention. For example, the sampling may occur by switching the ultrasound circuit between an on state and an off state for a short time interval during the activated period (e.g., DMI) at a frequency of pulsed Doppler signal packages tuned to maximum blood flow velocity, etc.

After determining whether to continue ultrasound monitoring (block 1214), method 1200 next samples blood flow velocity at the first sampling rate during a second time interval during a subsequent cardiac cycle at 1218. The second time interval occurs within the second cardiac cycle at a different time than the first time interval occurred during the first cardiac cycle. In other words, each time blood flow velocity is sampled, the sampling occurs at a different time interval within each subsequent cardiac cycle. By measuring blood flow velocity at different times within the cardiac waveform over a plurality of cardiac cycles, a complete blood flow velocity waveform may be interpolated utilizing each sample segment. Method 1200 repeats sampling for subsequent cardiac cycles as necessary and as reflected by decision blocks 1220, 1226, and third cardiac cycle sampling block 1224.

Figure 17:
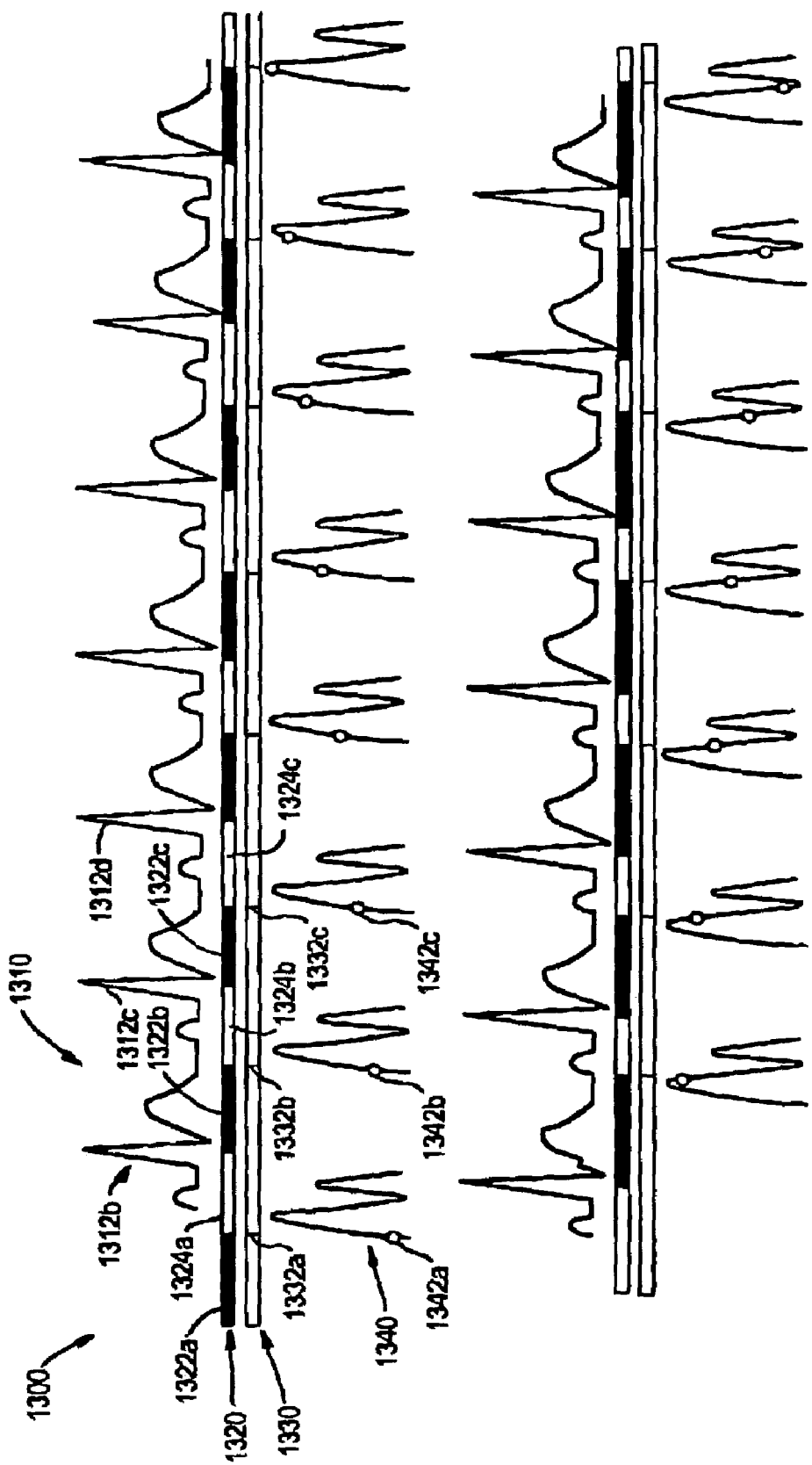
FIG. 17 is a graph illustrating the dual sampling ultrasound method of FIG. 16 in relation to a plurality of cardiac cycles.

FIG. 17 corresponds to and illustrates one embodiment of the dual ultrasound method 1200 as described above and illustrated in FIG. 16. FIG. 17 illustrates the equivalent time sampling of an E-wave of a tricuspid blood flow velocity waveform 1340 throughout the 16 exemplary cardiac cycles whereby a QRS complex 1312 of each cardiac cycle is used as a trigger event (i.e., the QRS complex triggers the start of a sampling delay interval as described below).

FIG. 17 includes the electrocardiogram waveform 1310, a Doppler activation time bar 1320, and a sampling time bar 1330. The Doppler measurement interval bar 1320 includes a plurality of sampling delay intervals 1322 wherein sampling is not performed, and a plurality of Doppler measurement intervals (DMIs) 1324 wherein sampling is performed. The sampling time bar 1330 includes each occurrence of a plurality of sampling time intervals 1332.

As the sampling time interval 1332 is extremely short, only a fraction of the flow waveform (e.g., a point of the waveform 1342) is sampled. The sampling time interval 1332 is initiated at the end of each sampling delay interval 1322. Sampling delay interval 1322 is triggered by detection of the QRS complex 1312 by any suitable method known in the art.

Every subsequent sampling delay interval 1322 is based upon the measurement of the preceding cardiac cycle interval (designated by 1/HR, i.e., being inversely proportional to the heart rate). If the heart rate is constant as illustrated in this FIG. 17, the next sampling delay interval 1322 is prolonged for a predetermined interval dT. Accordingly, in every subsequent cardiac cycle, another fraction of the E-wave is sampled, thereby sampling the entire E-wave at the end of the number of cardiac cycles predetermined to be sampled (16 in this example). Sampling precision depends on the size of dT. If dT is a very small percentage of 1/HR, the waveform sampling will last longer and the reconstructed waveform may be more accurate. However, this is only in the case when there is no marked variability of the heart rate.

For example, sampling delay interval 1322a may be triggered by a QRS complex of electrocardiogram waveform 1310. At the end of the sampling delay interval 1322a, the controller circuitry may activate the ultrasound circuit during DMI 1324a. At the onset of DMI 1324a, blood flow velocity is sampled at a first sampling rate during sampling time interval 1332a (see 1212 in FIG. 16), resulting in sampled point 1342a.

Following DMI 1324a, sampling delay interval 1322b occurs. Sampling delay interval 1322b, which is triggered by detection of QRS complex 1312b, is equal in time to sampling delay interval 1322a plus time dT. Following sampling delay interval 1322b, DMI 1324b occurs, which in turn triggers sampling time interval 1332b. During sampling time interval 1332b, blood flow velocity is sampled at the first sampling rate, thereby obtaining sampled point 1342b (see 1218 of FIG. 16). After acquiring all sampled points 1342, an equivalent E-wave waveform may be interpolated using techniques known in the art.

In some applications, precise interpolation of the blood flow velocity waveform is unnecessary. For example, mean blood flow velocity may be a very significant parameter for heart failure diagnostics and follow-up as well as in arrhythmia detection hemodynamic sensing. Accordingly, mean blood flow velocity may be calculated from every sampled point flow value.

Figure 18:
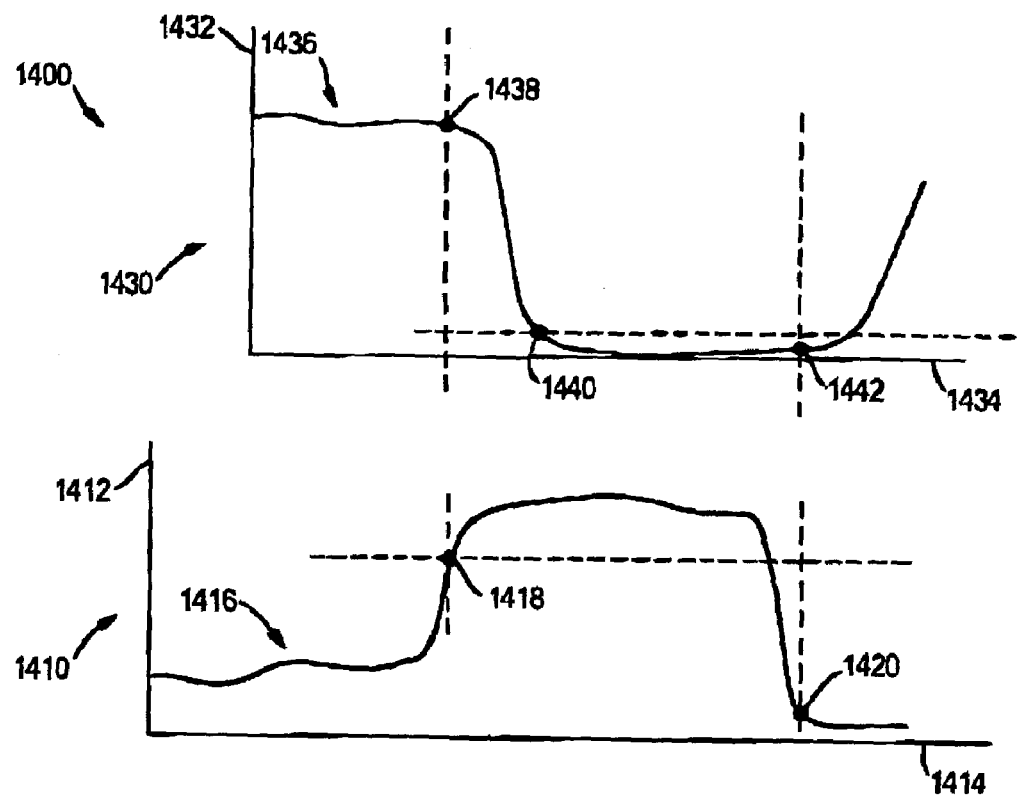
FIG. 18 is a graph illustrating the dual sampling ultrasound method of FIG. 16 in relation to detection of ventricular tachycardia.

FIG. 18 illustrates an embodiment that confirms a ventricular fibrillation attack utilizing the method described above and illustrated in FIG. 16. Graph 1410 illustrates heart rate 1412 as a function of time 1414 resulting in curve 1416, and graph 1430 illustrates mean blood flow velocity 1432 also as a function of time resulting in line 1436. The time scale is normally in seconds. Once a VT zone heart rate has been confirmed at 1418, the mean blood flow velocity is monitored at 1438 using techniques described above (see, e.g., 1212 of FIG. 16). A sudden drop in blood flow velocity (i.e., point 1440) confirms hemodynamically unstable arrhythmia. Termination of the unstable arrhythmia is detected at point 1420, where heart rate returns to normal, and confirmed by a return to normal mean blood flow velocity following point 1442.

Figure 19:
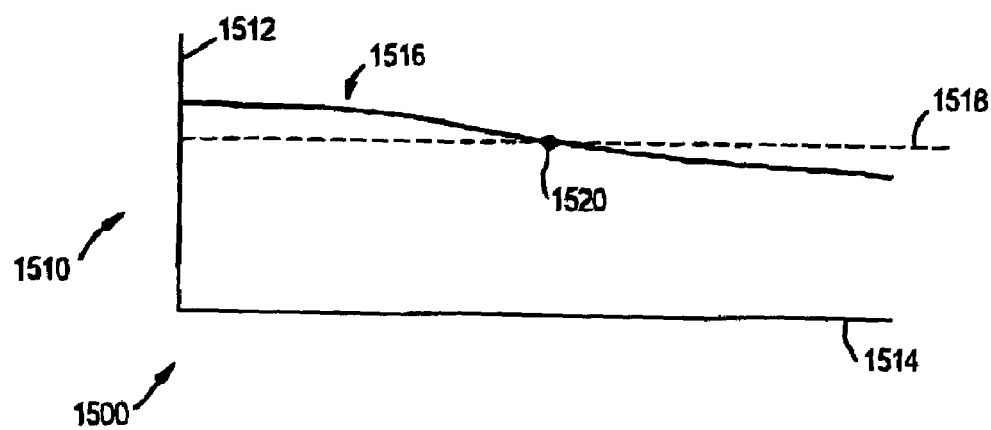
FIG. 19 is a graph illustrating the dual sampling ultrasound method of FIG. 16 in relation to mean blood flow velocity.

FIG. 19 illustrates mean blood flow velocity 1512 as a function of time 1514 during ventricular heart failure progression whereby restriction of ventricular filling slowly develops throughout a long period of time (e.g., several months). The time scale is therefore in days. A slow drop of the mean flow over time (i.e., curve 1516) develops and falls below the prescribed and preprogrammed value 1518 at 1520, which may then cause the IMD to issue an alarm to the patient. Follow-up using suitable drug therapies may be done with this system whereby an increase in the mean blood flow velocity may be accomplished. Method 1200 of FIG. 16 may be used to produce the mean blood flow velocity over an extended period of time while preserving battery power by not requiring blood flow velocity to be sampled for a long time interval during every cardiac cycle.

The complete disclosure of the patents, patent documents, and publications cited in the Background, Detailed Description of Embodiments, and elsewhere herein are incorporated by reference in their entirety as if each were individually incorporated.

The preceding specific embodiments are illustrative of the practice of the invention. It is to be understood, therefore, that other expedients known to those skilled in the art or disclosed herein may be employed without departing from the invention or the scope of the appended claims. For example, the present invention is not limited to ultrasound methods for measuring blood flow velocity and further one or more of the ultrasound methods and/or apparatus may be used in conjunction with one or more other methods and/or apparatus. The present invention is also not limited to ultrasound methods used in conjunction with IMDs per se, but may find further application as an external pacing and ultrasound monitoring device. The present invention further includes within its scope methods of making and using the IMDs described hereinabove.

What is claimed is:

1. An ultrasound method to monitor blood flow velocity for use in an implantable medical device, the method comprising:

activating an ultrasound circuit during a first portion of at least one cardiac cycle, wherein the ultrasound circuit is operable to provide pulsed Doppler signal packages during the first portion of the at least one cardiac cycle;

deactivating the ultrasound circuit during a second portion of the at least one cardiac cycle, wherein the ultrasound circuit is inoperable to provide pulsed Doppler signal packages during the second portion of the at least one cardiac cycle; and switching the ultrasound circuit between an on state where pulsed Doppler signal packages are provided and an off state where pulsed Doppler signal packages are not provided during the first portion of the at least one cardiac cycle at a first sampling rate.

2. The method of claim 1, wherein the method further comprises:
switching the ultrasound circuit between the on state and off state at the first rate during at least a first time period of the first portion of the at least one cardiac cycle; and
switching the ultrasound circuit between the on state and the off state at a second rate during at least a second time period of the first portion of the at least one cardiac cycle.

3. The method of claim 1, wherein the pulsed Doppler signal packages are provided at a region proximate a tricuspid valve.

4. The method of claim 1, wherein the method further comprises:
switching the ultrasound circuit between the on state and off state at the first rate during at least the first portion of a first cardiac cycle; and
switching the ultrasound circuit between the on state and the off state during a first portion of at least another cardiac cycle at a second rate.

5. The method of claim 4, wherein the first rate is associated with a detection mode, and further wherein the second rate is associated with a measurement mode.

6. The method of claim 5, wherein the detection mode is configured to detect an atrial blood flow velocity filling wave, and further wherein the measurement mode is configured to determine an acceleration of a diastolic blood flow velocity filling wave.

7. The method of claim 4, wherein the method further comprises:
detecting a rate switching event; and
switching from the first rate to the second rate based on the detection of the rate switching event, wherein the second rate is different from the first rate.

8. The method of claim 7, wherein detecting the rate switching event further comprises:
monitoring a physiological parameter of a patient and
detecting the rate switching event based on the monitored physiological parameter.

9. The method of claim 8, wherein the physiological parameter comprises patient activity.

10. The method of claim 8, wherein the physiological parameter comprises a heart rate.

11. The method of claim 7, wherein the method further comprises switching from the second rate to the first rate based on the detection of an additional rate switching event.

12. An ultrasound method, comprising:
activating an ultrasound circuit during at least a first time interval, wherein the ultrasound circuit is operable to provide pulsed Doppler signal packages during the first time interval;
deactivating the ultrasound circuit during at least a second time interval, wherein the ultrasound circuit is inoperable to provide pulsed Doppler signal packages during the second time interval; and
switching the ultrasound circuit between an on state where pulsed Doppler signal packages are provided and an off state where pulsed Doppler signal packages are not provided during at least a portion of the first time interval at a first rate.

13. The method of claim 12, wherein the first time interval and the second time interval fall within a cardiac cycle.

14. The method of claim 12, wherein the method further comprises tuning a frequency of the provided pulsed Doppler signal packages based on a predetermined maximum blood flow velocity.

15. The method of claim 12, wherein pulsed Doppler signal packages are provided at a region proximate a tricuspid valve.

16. The method of claim 12, wherein the method further comprises switching between the on state and the off state during at least another portion of the first time interval at a second rate.

17. The method of claim 16, wherein switching between the on state and the off state at the first rate occurs during one or more cardiac cycles, and further wherein switching between the on state and the off state at the second rate occurs during one or more different cardiac cycles.

18. The method of claim 16, wherein the first rate is associated with a detection mode, wherein the second rate is associated with a measurement mode, and further wherein the first rate is slower than the second rate.

19. The method of claim 18, wherein the detection mode is configured to detect an atrial blood flow velocity filling wave, and further wherein the measurement mode is configured to determine an acceleration of a diastolic blood flow velocity filling wave.

20. The method of claim 16, wherein the method further comprises:
detecting a rate switching event; and
switching from the first rate to the second rate based on the detection of the rate switching event.

21. The method of claim 20, wherein the method further comprises switching from the second rate to the first rate based on the detection of an additional rate switching event.

22. The method of claim 20, wherein detecting the rate switching event further comprises;
monitoring a physiological parameter of a patient; and
detecting the rate switching event based on the monitored physiological parameter.

23. The method of claim 22, wherein the physiological parameter comprises patient activity.

24. The method of claim 22, wherein the physiological parameter comprises a heart rate.

25. An ultrasound method to monitor blood flow velocity for use in an implantable medical device, comprising:
activating an ultrasound circuit during at least a first time interval, wherein the ultrasound circuit is operable to provide pulsed Doppler signal packages during the first time interval;
deactivating the ultrasound circuit during at least a second time interval, wherein the ultrasound circuit is inoperable to provide pulsed Doppler signal packages during the second time interval;
switching the ultrasound circuit between an on state where pulsed Doppler signal packages are provided and an off state where pulsed Doppler signal packages are not provided during at least a portion of the first time interval at a first rate; and
switching the ultrasound circuit between the on state and the off state during at least another portion of the first time interval at a second rate.

26. The method of claim 25, wherein the method further comprises tuning a frequency of the provided pulsed Doppler signal packages based on a predetermined maximum blood flow velocity.

27. The method of claim 25, wherein pulsed Doppler signal packages am provided at a region proximate a tricuspid valve.

28. An implantable medical apparatus, comprising:
an ultrasound circuit operable to provide pulsed Doppler signal packages; and
controller circuitry in communication with the ultrasound circuit, the controller circuitry operable to:
activate the ultrasound circuit during at least a first time interval, wherein the ultrasound circuit is operable to provide pulsed Doppler signal packages during the first time interval;
deactivate the ultrasound circuit during at least a second time interval, wherein the ultrasound circuit is inoperable to provide pulsed Doppler signal packages; and
switch the ultrasound circuit between an on state where pulsed Doppler signal packages are provided and an off state where pulsed Doppler signal packages are not provided during at least a portion of the first time interval at a first rate.

29. The apparatus of claim 28, wherein the controller circuitry is further operable to switch the ultrasound circuit between the on state and the off state during at least another portion of the first time interval at a second rate.

30. The apparatus of claim 29, wherein the apparatus further comprises a detection sensor in communication with the controller circuitry, wherein the detection sensor is operable to detect a rate switching event, wherein the controller circuitry is further operable to switch from the first rate to the second rate based on the detection of the rate switching event.

31. The apparatus of claim 29, wherein the controller circuitry is further operable to:
switch between an on state and an off state at the first rate during one or more cardiac cycles; and
switch between an on state and an off state at the second rate during one or more different cardiac cycles.

32. The apparatus of claim 29, wherein the first time interval and the second time interval fall within a cardiac cycle.

33. The apparatus of claim 29, wherein the first rate is associated with a detection mode, wherein the second rate is associated with a measurement mode, and further wherein the first rate is slower than the second rate.

34. The apparatus of claim 33, wherein the controller circuitry while in detection mode is operable to detect an atrial blood flow velocity filling wave, and further wherein the controller circuitry while in measurement mode is operable to determine an acceleration of a diastolic blood flow velocity filling wave.

35. The apparatus of claim 30, wherein the controller circuitry is further operable to switch from the second rate to the first rate based on the detection of an additional rate switching event.

36. The apparatus of claim 30, wherein the detection sensor is further operable to:
detect a physiological parameter of a patient; and
detect the rate switching event based on the detected physiological parameter.

37. The apparatus of claim 36, wherein the detection sensor comprises an accelerometer, and further wherein the physiological parameter comprises patient activity.

38. The apparatus of claim 36, wherein the detection sensor comprises a heart rate sensor, and further wherein the physiological parameter comprises a heart rate.

39. The apparatus of claim 28, wherein the ultrasound circuit is operable to provide pulsed Doppler signal packages at a frequency based on a predetermined maximum blood flow velocity.

40. The apparatus of claim 28, wherein the apparatus further comprises an implantable lead in communication with the ultrasound circuit, wherein the implantable lead is operable to deliver pulsed Doppler signal packages to a region proximate a tricuspid valve.

* * * * *

UNITED STATES PATENT AND TRADEMARK OFFICE
CERTIFICATE OF CORRECTION

| | | |
|---|---|---|
| PATENT NO. | : 7,037,266 B2 | Page 1 of 1 |
| APPLICATION NO. | : 10/131256 | |
| DATED | : May 2, 2006 | |
| INVENTOR(S) | : Bozidar Ferek-Petric | |

It is certified that error appears in the above-identified patent and that said Letters Patent is hereby corrected as shown below:

Title page item (75) Inventors: delete "Bozidar Ferek-Petric and insert --Bozider Ferek-Petric--

Signed and Sealed this

Third Day of April, 2007

JON W. DUDAS
*Director of the United States Patent and Trademark Office*